United States Patent [19]
Magda et al.

[11] Patent Number: 5,837,866
[45] Date of Patent: Nov. 17, 1998

[54] PHOSPHORAMIDITE DERIVATIVES OF MACROCYCLES

[75] Inventors: Darren Magda, Cupertino, Calif.; Jonathan L. Sessler, Austin, Tex.; Shaun P. Crofts, Campbell, Calif.

[73] Assignees: Board of Regents, The University of Texas, Austin, Tex.; Pharmacyclics, Inc., Sunnyvale, Calif.

[21] Appl. No.: 862,778

[22] Filed: May 23, 1997

Related U.S. Application Data

[63] Continuation-in-part of Ser. No. 614,638, Mar. 13, 1996, Pat. No. 5,633,354, which is a continuation of Ser. No. 487,722, Jun. 7, 1995, Pat. No. 5,565,552, which is a continuation-in-part of Ser. No. 310,501, Sep. 21, 1994, Pat. No. 5,567,587.

[51] Int. Cl.[6] .......................... C07D 187/22; C07F 7/00; C07F 9/6524
[52] U.S. Cl. ................... 540/145; 536/17.1; 536/17.3; 536/17.4; 540/472
[58] Field of Search ................... 540/145, 472; 536/17.1, 17.3, 17.4

[56] References Cited

U.S. PATENT DOCUMENTS

| | | | |
|---|---|---|---|
| 4,318,825 | 3/1982 | Frame | 252/428 |
| 4,647,447 | 3/1987 | Gries et al. | 524/9 |
| 4,835,263 | 5/1989 | Nguyen et al. | 536/27 |

(List continued on next page.)

FOREIGN PATENT DOCUMENTS

| | | |
|---|---|---|
| 0111418 | 6/1984 | European Pat. Off. . |
| 0196515 | 10/1986 | European Pat. Off. . |
| 0 214 908 | 3/1987 | European Pat. Off. . |
| 0233701 A2 | 8/1987 | European Pat. Off. . |
| 2 697 254 | 4/1994 | France . |
| WO 90/02747 | 3/1990 | WIPO . |
| 90/01208 | 8/1990 | WIPO . |
| WO 90/10633 | 9/1990 | WIPO . |
| 91/19730 | 12/1991 | WIPO . |
| 92/01781 | 2/1992 | WIPO . |
| WO 93/14093 | 7/1993 | WIPO . |
| WO 94/09003 | 4/1994 | WIPO . |
| WO 94/29316 | 12/1994 | WIPO . |
| WO 95/21845 | 8/1995 | WIPO . |

OTHER PUBLICATIONS

Shiokhet et al., Chemical Abstracts, vol. 116, abstract 119638, 1992.

Buchler et al., Chemical Abstracts, vol. 101, abstract 64923, 1984.

Ogoshi et al. "New Mode of Porphyrin Complexation with Nucleobase," *J. Am. Chem. Soc.*, 113:8181–8183 (1991).

Mestre et al. "Preparation and Nucelase Activity of Hybrid 'Metallotris(methylpyridinium)porphyrin Oligonucleotide' Molecules Having a 3'–Loop for Protection against 3'–Exonucleases," *Bioconjugate Chem.*, 6:466–472 (1995).

Abid et al., "Lanthanide Complexes of Some Macrocyclic Schiff Bases Derived from Pyridine–2,6–dicarboxaldehyde and $\alpha,\Omega$–Primary Diamines", *Inorg. Chim. Acta*, 95:119–125, 1984.

Acholla et al., "Binucleating Tetrapyrrole Macrocycles", *J. Am. Chem. Soc.*, 107:6902–6908, 1985.

Acholla et al., "A Binucleating Accordian Tetrapyrrole Macrocycle", *Tetrahedron Lett.*, 25:3269–3270, 1984.

Ansell, "X–Ray Crystal Structure of the Pentagonal Bipyramidal Nickel(11) Complex [Ni$^{11}$(L)(H$_2$O)$_2$](BF$_4$)$_2$ and the Selective Stabilization of the Nickel(1) Oxidation State by a Quinquedentate Macrocyclic Ligand", *J. Chem. Soc., Chem. Commun.*, pp. 546–547, 1982.

(List continued on next page.)

*Primary Examiner*—Richard L. Raymond
*Attorney, Agent, or Firm*—Jacqueline S. Larson

[57] ABSTRACT

The invention is directed to phosphoramidite derivatives of macrocycles, such as porphyrins and expanded porphyrins, including sapphyrins and texaphyrins. The phosphoramidite derivatives are useful as intermediates in the preparation of macrocycle-oligonucleotide conjugates.

12 Claims, 8 Drawing Sheets

U.S. PATENT DOCUMENTS

| | | | |
|---|---|---|---|
| 4,878,891 | 11/1989 | Judy et al. | 604/5 |
| 4,880,088 | 11/1989 | Lauffer | 128/654 |
| 4,883,790 | 11/1989 | Levy et al. | 540/145 |
| 4,899,755 | 2/1990 | Lauffer et al. | 128/654 |
| 4,915,683 | 4/1990 | Sieber | 604/4 |
| 4,935,498 | 6/1990 | Sessler et al. | 534/15 |
| 4,959,363 | 9/1990 | Wentland | 514/235 |
| 4,977,177 | 12/1990 | Bommer et al. | 514/410 |
| 5,021,236 | 6/1991 | Gries et al. | 424/9 |
| 5,030,200 | 7/1991 | Judy et al. | 604/5 |
| 5,041,078 | 8/1991 | Matthews et al. | 604/4 |
| 5,120,411 | 6/1992 | Sessler et al. | 204/157.15 |
| 5,141,911 | 8/1992 | Meunier et al. | 502/159 |
| 5,159,065 | 10/1992 | Sessler et al. | 534/15 |
| 5,162,509 | 11/1992 | Sessler et al. | 534/15 |
| 5,242,797 | 9/1993 | Hirschfeld | 435/7 |
| 5,252,720 | 10/1993 | Sessler et al. | 534/11 |
| 5,256,399 | 10/1993 | Sessler et al. | 424/9 |
| 5,272,056 | 12/1993 | Burrows et al. | 435/6 |
| 5,272,142 | 12/1993 | Sessler et al. | 514/185 |
| 5,292,414 | 3/1994 | Sessler et al. | 204/157.5 |
| 5,302,714 | 4/1994 | Sessler et al. | 540/472 |
| 5,369,101 | 11/1994 | Sessler et al. | 534/13 |
| 5,371,199 | 12/1994 | Therien et al. | 534/11 |
| 5,432,171 | 7/1995 | Sessler et al. | 514/185 |
| 5,439,570 | 8/1995 | Sessler et al. | 254/157.17 |
| 5,451,576 | 9/1995 | Sessler et al. | 514/185 |
| 5,457,183 | 10/1995 | Sessler et al. | 534/11 |
| 5,457,195 | 10/1995 | Sessler et al. | 540/472 |
| 5,475,104 | 12/1995 | Sessler et al. | 540/472 |
| 5,504,205 | 4/1996 | Sessler et al. | 540/474 |
| 5,525,325 | 6/1996 | Sessler et al. | 424/9.6 |
| 5,530,123 | 6/1996 | Sessler et al. | 540/474 |
| 5,543,514 | 8/1996 | Sessler et al. | 540/472 |
| 5,559,207 | 9/1996 | Sessler et al. | 530/300 |
| 5,565,552 | 10/1996 | Magda et al. | 534/11 |
| 5,567,687 | 10/1996 | Magda et al. | 514/44 |
| 5,569,759 | 10/1996 | Sessler et al. | 540/472 |
| 5,583,220 | 12/1996 | Sessler et al. | 540/472 |
| 5,586,463 | 12/1996 | Sessler et al. | 534/15 |
| 5,587,371 | 12/1996 | Sessler et al. | 514/185 |
| 5,587,478 | 12/1996 | Sessler et al. | 540/474 |
| 5,591,422 | 1/1997 | Hemmi et al. | 424/9.362 |
| 5,594,136 | 1/1997 | Sessler et al. | 540/472 |
| 5,595,726 | 1/1997 | Magda et al. | 424/9.61 |
| 5,599,923 | 2/1997 | Sessler et al. | 540/145 |
| 5,599,928 | 2/1997 | Hemmi et al. | 540/474 |
| 5,601,802 | 2/1997 | Hemmi et al. | 424/9.363 |
| 5,607,924 | 3/1997 | Magda et al. | 514/44 |
| 5,622,945 | 4/1997 | Sessler et al. | 514/185 |
| 5,622,946 | 4/1997 | Sessler et al. | 514/185 |
| 5,632,970 | 5/1997 | Sessler et al. | 424/9.61 |
| 5,633,354 | 5/1997 | Magda et al. | 534/15 |
| 5,672,490 | 9/1997 | Sessler et al. | 435/91.1 |

OTHER PUBLICATIONS

Bauer et al., "Sapphyrins: Novel Aromatic Pentapyrrolic Macrocycles", *J. Am. Chem. Soc.*, 105:6429–6436, 1983.

Broadhurst et al., "Preparation of Some Sulphur–containing Polypyrrolic Macrocycles. Sulphur Extrusion from a meso–Thiaphlorine", *J. Chem. Soc., Chem. Commun.* pp. 807–809, 1970.

Broadhurst et al., "18–and 22–π–Electron Macrocycles Containing Furan, Pyrrole, and Thiophen Rings", *J. Chem. Soc., Chem. Commun.* pp. 1480–1482, 1969.

Broadhurst et al., "New Macrocyclic Aromatic Systems Related to Porphins", *J. Chem. Soc., Chem. Commun.* pp. 23–24, 1969.

Broadhurst et al., "The Synthesis of 22 π–Electron Macrocycles. Sapphyrins and Related Compounds", *J. Chem. Soc. Perkin Trans.*, 1:2111–2116, 1972.

Cuellar et al., "Synthesis and Characterization of Metallo and Metal–Free Octaalkylphthalocyanines and Uranyl Decaalkysuperphthalocyanines", *Inorg. Chem.*, 20:3766–3770, 1981.

Day et al., "Large Metal Ion–Centered Template Reactions. A Uranyl Complex of Cyclopentakis (2–iminoisoindoline)", *J. Am. Chem. Soc.*, 97:4519–4527, 1975.

De Cola et al., "Hexaaza Macrocyclic Complexes of the Lanthanides", *Inorg. Chem.*, 25:1729–1732, 1986.

Dougherty, "Photosensitizers: Therapy and Detection of Malignant Tumors", *Photochem. Photobiol.*, 45:879–889, (1987).

Gosmann et al., "Synthesis of a Fourfold Enlarged Porphyrin with an Extremely Large, Diamagnetic Ring–Current Effect", *Angew. Chem., Int. Ed Engl.*, 25:1100–1101, (1986).

Gossauer, "Synthesis of Some Unusual Polypyrrole Macrocycles", *Bull Soc. Chim. Belg.*, 92:793–795, (1983).

Knubel et al., "Biomimetic Synthesis of an Octavinylogous Porphyrin with an Aromatic [34] Annulene System", *Angew. Chem., Int. Ed. Engl.*, 27:1170–1172, 1988.

Lauffer, "Paramagnetic Metal Complexes as Water Proton Relaxation Agents for NMR Imaging: Theory and Design", *Chem. Rev.*, 87:901–927, 1987.

LeGoff et al., "Synthesis of a [1,5,1,5] Platyrin, a 26 π–Electron Tetrapyrrolic Annulene", *J. Org. Chem.*, 52:710–711, 1987.

Marks et al., "Large Metal Ion–Centered Template Reactions. Chemical and Spectral Studies of the Superphthalocyanine Dioxocyclopentakis (1–iminoisoindolinato) uranium (VI) and Its Derivatives", *J. Am. Chem. Soc.*, 100:1695–1705, 1978.

Rexhausen et al., "The Synthesis of a New 22 π–Electron Macrocycle: Pentaphyrin", *J. Chem. Soc., Chem. Commun.*, p. 275, 1983.

Sessler et al., "Synthesis and Crystal Structure of a Novel Tripyrrane–Containing Porphyrinogen–like Macrocycle", *J. Org. Chem.*, 52:4394–4397, 1987.

Sessler et al., "The Coordination Chemistry of Planar Pentadentate Porphyrin–Like Ligands", *Comm. Inorg. Chem.*, 7:333–350, 1988.

Sessler et al., "An Expanded Porphyrin: The Synthesis and Structure of a New Aromatic Pentadentate Ligand", *J. Am. Chem. Soc.*, 110;5586–5588, 1988.

Tweedle et al., "Principles of Contrast–Enhanced MRI", in Magnetic Resonance Imaging, 2nd ed. Partain, et al, Eds., W. B. Saunders: Philadelphia, vol. I (1988) 793–809.

Vogel et al., "Porphycene—a Novel Porphin Isomer", *Angew. Chem., Int. Ed. Engl.*, 25:257–259, 1986.

Vogel et al., "2,7,12,17–Tetrapropylporphycene—Counterpart of Octaethylporphyrin in the Porphycene Series", *Angew. Chem., Int. Ed. Engl.*, 26:928–931, 1987.

Sessler et al., "A Water–Soluble Gadolinium (III) Complex Derived from a New Pentadentate Expanded Porphyrin Ligand", *Inorg. Chem.*, 28:3390–3393, 1989.

Sessler et al., "Binding of Pyridine and Benzimidazole to a Cadmium Expanded Porphyrin: Solution and X–ray Structural Studies", *Inorg. Chem.*, 28:1333–1341, 1989.

Harriman et al., "Metallotexaphyrins: A New Family of Photosensitisers for Efficient Generation of Singlet Oxygen", *J. Chem. Soc., Chem. Commun.*, 314–316, 1989. Submitted as A32 in 1449 for UTSB:458.

Sessler et al., "Expanded Porphyrins: The synthesis and Metal Binding Properties of Novel Tripyrrane–Containing Macrocycles", *J. Coord. Chem.*, 18:99–104, 1988.

Sessler et al., "The Synthesis and Structure of a Novel 22 π–Electron Aromatic Pentadentate Macrocyclic Ligand: An Expanded Porphyrin", Toronto ACS Meeting, Jun. 1988. USA.

Sessler et al., "A Water–Stable Gadolinium (III) Complex Derived from a New Pentadentate", *Chem. Absts.*, 111:720, abstract No. 125716e, Oct. 2, 1989.

Stinson, "Unusual Porphyrin Analog Promises Many Applications", *Chemical and Engineering News*, pp. 26–27, Aug. 8, 1988.

Sessler et al., "Tripyrroledimethine–derived (Texaphyrin–type) Macrocycles: Potential Photosensitizers Which Absorb in the Far–red Spectral Region", *SPIE, Optical Methods for Tumor Treatment and Early Diagnosis: Mechanism and Technique*, 1426:318–329, 1991.

Sessler et al., "'Texaphryin': A Novel 22 π–Electron Aromatic Pentadentate Macrocyclic Ligand", *ACS meeting*, Los Angeles, Sep. 1988.

Sessler and Burrell, "Expanded Porphyrins," *Topics in Current Chemistry*, 161:180–273, 1991.

Sessler et al., "Synthesis and Structural Characterization of Lanthanide(III) Texaphyrins," *Inorganic Chemistry*, 32(14):3175–3187, 1993.

"2–Äthylamino–2–methyl–propanol–(1)", " *Beilstein's Handbuch*, 4;785, 1950.

"Tentative Rules for Carbohydrate Nomenclature Part 1 (1969)," *Handbook of Biochemistry and Molecular Biology*, 3rd ed., Fasman, Ed., CRC Press, Cleveland, Ohio, pp. 100–102.

Sessler et al., "Preparaton of Lanthanide (III) Texaphyrin Complexes and Their Applications to Magnetic Resonance Imaging and Photodynamic Therapy," *Abstracts of Papers*, Part 1, 204th ACS National Meeting, Aug. 23–28, 1992, Washington, DC.

Sessler et al., "Synthesis and Applications of Schiff–Base Derived Expanded Porphyrins," *Abstracts of Papers*, Part 1, 204th ACS National Meeting, Aug. 23–28, 1992, Washington, DC.

Sessler, Jonathan L., "Texas–Sized Molecule," *Discovery*, 13(1):44–49, 1993.

Sessler et al., "Photodynamic Inactivation of Enveloped Viruses Using Sapphyrin, α 22 π–Electron Expanded Porphyrin: Possible Approaches to Prophylactic Blood Purification Protocols," *SPIE Photodynamic Therapy: Mechanisms II*. 1203:233–245, 1990.

Maiya et al., "Ground–and Excited–State Spectral and Redox Properties of Cadmium(II) Texaphyrin," *Journal of Physical Chemistry*, 93(24):8111–8115, 1989.

Sessler et al., "Texaphyrins: Synthesis and Applications," *Accounts of Chemical Research*, 27(2):43–50, 1994.

Leff, "Texas 'Son–of–porphyrin' Molecule Lassos Europium to Kill Drug Resistance Gene," *BioWorld Today*, 5(156):1, 1994.

Young et al., "Preclinical Evaluation of Gadolinium (III) Texaphyrin Complex. A New Paramagnetic Contrast Agent for Magnetic Resonance Imaging," *Investigative Radiology*, 29(3):330–338, 1994.

Dietrich et al., "Proton Coupled Membrane Transport of Anions Mediated by Cryptate Carriers," *J. Chem. Soc. Chem. Comm.*, 1988, 11:691–692.

Dixon et al., "Molecular Recognition: Bis–Acylguanidiniums Provide a Simple Family of Receptors for Phosphodiesters," *J. A. Chem. Soc.*,1992, 114:365–366.

Furuta et al., "Enhanced Transport of Nucleosides and Nucleoside Analogues with Complementary Base–Pairing Agents," *Journal of the American Chemical Society*, 1991, 113:4706–4707.

Galán et al., "A Synthetic Receptor for Dinucleotides," *J. Am. Chem. Soc.*, 1991, 113:9424–9425.

Galán et al., "Selective Complexation of Adenosine Monophosphate Nucleotides By Rigid Bicyclic Guanidinium Abiotic Receptors," *Tetrahedron Letters*, 32(15):1827–1830, 1991.

Hisatome et al., "Porphyrins Coupled with Nucleoside Bases. Synthesis and Characterization of Adenine–and Thymine–Porphyrin Derivatives," *Chemistry Letters*, 1990, 2251–2254.

Hosseini et al., "Multiple Molecular Recognition and Catalysis. A Multifunctional Anion Receptor Bearing an Anion Binding Site, an Intercalating Group, and a Catalytic Site for Nucleotide Binding and Hydrolysis," *J. Am. Chem. Soc.*, 1990, 112:3896–3904.

Hosseini et al., "Multiple Molecular Recognition and Catalysis. Nucleotide Binding and ATP Hydrolysis by a Receptor Molecule Bearing an Anion Binding Site, an Intercalcator Group, and a Catalytic Site," *J. Chem. Soc. Chem. Commun.*, 1988, 9:596–598.

Kimura et al., "A Study of New Bis(macrocylic polyamine) Ligands as Inorganic and Organic Anion Receptors," *J. Org. Chem.*, 1990, 55(1):46–48.

Kimura et al., "Macrocyclic Polyamines as Biological Cation and Anion Complexones: An Application to Calculi Dissolution," *Topics in Current Chemistry, 128, Biomimetic and Bioorganic Chemistry*, VII+265P, Springer–Verlag, Berlin, West Germany, pp. 133, 142, 1985.

Li and Diederich, "Carriers for Liquid Membrane Transport of Nucleotide 5'–Triphosphates," *J. Org. Chem.*, 1992, 47:3449–3454.

Marks and Stojakowvic, "Large Metal Ion–Centered Template Reactions. Chemical and Spectral Studies of the Superphthalocyanine Dioxocyclopentakis (1–iminoisoindolinato)uranium(VI) and Its Derivatives," *J. Am. Chem. Soc.*, 1978, 1695–1705.

Schmidtchen, "A Non–Macrocyclic Host for Binding Organic Phosphates in Protic Solvents," *Tetrahedron Letters*, 1989, 30(34):4493–4496.

Seel and Vogtle, "Molecular Recognition and Transport of Nucleobases—Superiority of Macrobicyclic Host Molecules," *Angew. Chem. Int. Ed. Engl.*, 1991, 30(4):442–444.

Sessler et al., "Anion Binding: A New Direction in Porphyrin–Related Research," *Pure & Applied Chem.*, 65(3):393–398, 1993.

Sessler et al., "Cytosine Amine Derivatives," *J. Org. Chem.*, 1992, 47:826–834.

Aoyama et al., "Multi–Point Interaction of Phosphates with Protonated Pyridylporphyrin. Discrimination of Monoalkyl and Dialkyl Phosphates," *Chemistry Letters*, 1241–1244 (1991).

Claude et al., "Binding of Nucleosides, Nucleotides and Anionic Planar Substrates by Bis–Intercaland Receptor Molecules," *J. Chem. Soc. Chem. Commun.*, 1991, 17:1182–1185.

Cramer et al., "Synthesis and Structure of the Chloride and Nitrate Inclusion Complexes of [16–Pyrimidinium crown–4]," *J. Am. Chem. Soc.*, 1991, 113:7033–7034.

Tabushi et al., "Lipophilic Diammonium Cation Having a Rigid Structure Complementary to Pyrophosphate Dianions of Nucleotides. Selective Extraction and Transport of Nucleotides," *J. Am. Chem. Soc.*, 1981, 103:6152–6157.

Tohda et al., "Ligand Membrane Electrode for Guanosine Nucleotides Using a Cytosine–Pendant Triamine Host as the Sensory Element," *Analytical Chemistry*, 1992, 64(8):960–964.

Nam–Chiang Wang et al., "Pyrrole chemistry. XVII. Alkylation of the pyrrolyl ambident anion," *Can. J. Chem.*, 55:4112–4116, 1977.

T.D. Mody et al., "Lutetium (III) Texaphyrin: A Novel Photodynamic Therapy Agent," Abstract, *22nd Annual American Society for Photobiology*, Scottsdale, AZ, Jun. 25–29, 1994.

Sessler et al., "Gadolinium (III) Texaphyrin: A Novel MRI Contrast Agent," *Journal of the American Chemical Society*, 115(2):10,368–10,369,1993.

Iverson et al., "Interactions Between Expanded Porphyrins and Nucleic Acids," *Pure Applied Chemistry*, 66(4):845–850, 1994.

Matthews et al., "Inactivation of Viruses with Photoactive Compounds," *Blood Cells*, 18(1):75–89, 1992.

Ehrenberg et al., "Spectroscopy, Photokinetics and Cellular Effect of Far–Red and Near Infrared Absorbing Photosensitizers," *Proc. SPIE—Int. Soc. Opt. Eng 1992, 1645 (Proc. Opt. Mehods Tumor Treat. Dect.: Mech. Tech. Photodyn. Ther..*, 259–263, 1992.

Thaller et al., "Potential Use of Radiolabelled Porphyrins for Tumor Scanning," *Porphyrin Photosensitization*, Kessel and Dougherty, Eds., Plenum Press, New York and London, Publisher, pp. 265–278, 1981.

Magda et al., "Site–Specific Hydrolysis of RNA by Europium (III) Texaphyrin Conjugated to a Synthetic Oligodeoxyribonucleotide," *Journal of the American Chemical Society*, 116(16):7439–7440, 1994.

Koenig et al., "PDT of Tumor–Bearing Mice using Liposome Delivered Texaphyrins," Internatoinal Conference, Milan, Itay, Biosis citation only, Jun. 24–27, 1992.

Goodchild, John, "Conjugates of Oligonucleotides and Modified Oligonucleotides: A Review of Their Synthesis and Properties," *Bioconjugate Chemistry*, 1(3):165–187, 1990.

Kobayashi et al., "Uptake of Cholorphyll–Derivatives by Cellular Nuclei and Mitochondria," *Photomed. Photobiol.*, 15:75–84, 1993.

Brown and Truscott, "New Light on Cancer Therapy," *Chemistry in Britain*, 955–958, 1993.

Lin et al., "Use of EDTA Derivatization to Characterize Interactions between Oligodeoxyribonucleoside Methylphosphonates and Nucleic Acids," *Biochemistry*, 28:1054–1061, 1989.

Strobel and Dervan, "Cooperative Site Specific Binding of Oligonucleotides to Duplex DNA," *Journal of the American Chemical Society*, 111(18):7286–7287, 1989.

Dreyer and Dervan, "Sequence–specific Cleavage of Single–Stranded DNA: Oligodeoxynucleotide–EDTA•Fe(II)," *Proc. Natl. Acad. Sci. USA*, 82:968–972, 1985.

Doan et al., "Sequence–targeted Chemical Modifications of Nucleic Acids by Complementary Oligonucleotides Covalently Linked to Porphyrins," *Nucleic Acids Research*, 15(21):8643–8659, 1987.

Dervan, Peter B., "Design of Sequence–Specific DNA–Binding Molecules," *Science*, 232;464–471, 1986.

Groves and Farrell, "DNA Cleavage by a Metal Chelating Tricationic Porphyrin," *J. A. Chem. Soc.*,111;4998–5000, 1989.

Fiel, Robert J., "Porphyrin–Nucleic Acid Interactions: A Review," *Journal of Biomolecular Structure & Dynamics*, 6(6):1259–1275, 1989.

Vlassov et al., "Photoactivatable Porphyrin Oligonucleotide Derivatives for Sequence Specific Chemical Modification and Cleavage of DNA," *Nucleosides & Nucleotides*, 10(1–3): 641–643, 1991.

Zuk et al., "Pharmacokinetic and Tissue Distribution Studies of the Photosensitizer bis(Di–Isobutyl Octadecysiloxy) Silicon 2,3–Naphthalocyanine (isoBosinc) in Normal and Tumor–Bearing Rats," *Photochemistry and Photobiology*, 59(1):66–72, 1994.

Lee et al., "Interaction of Psoralen–Derivatized Oligodeoxyribonucleoside Methylphosphonates with Single–Stranded DNA," *Biochemistry*, 27:3197–3203, 1988.

Bhan and Miller, "Photo–Cross Linking of Psoralen–Derivatized Oligonucleoside Methylphosphonates to Single–Stranded DNA," *Bioconjugate Chem.*, 1:82–88, 1990.

Boutorine et al., "Fulleren–Oligonucleotide Conjugates: Photo–Induced Sequence Specific DNA Cleavage", *Agnew. Chem. Int. Ed., Engl.*, 33(23/24):2462–2465, 1994.

Dolphin et al., "Porphocyanine: An Expanded Tetrapyrrolic Macrocycle," *J. Am. Chem. Soc.*, 115:9301–9302, 1993.

Ehrenberg et al., "The Binding and Photosensitization Effects of Tetrabenzoporphyrins and Texaphyrin in Bacterial Cells," *Lasers in Medical Science*, 8;197–203, 1993.

Le Doan et al., "Sequence–Targeted Photochemical Modifications of Nucleic Acids by Complementary Oligonucleotides Covalently Linked to Porphyrins," *Bioconjugate Chem.*, 1:108–113, 1990.

Le Doan et al., "Sequence–Specific Recognition, Photocrosslinking and Cleavage of the DNA Double Helix by an Oligo–[α]–Thymidylate Covalently Attached to an Azidoproflavine," *Nucleic Acids Res.*, 15:7749–7760, 1987.

Levina et al., "Photomodification of RNA and DNA Fragments by Oligonucleotide Reagents Bearing Arylazide Groups," *Biochimie*, 75:25–27, 1993.

Mastruzzo et al., "Targeted Photochemical Modification of HIV–Derived Oligoribonucleotides by Antisense Oligodeoxynucleotides Linked to Porphyrins," *Photochem. Photobiol.*, 60(4):316–322, 1994.

Fedorova et al., "Palladium(II)–Coproporphyrin I as a Photoactivable Group in Sequence–Specific Modification of Nucleic Acids by Oligonucleotide Derivatives," *FEB Lett.*, 259(2);335–337, 1990.

Morgan and Skalkos, "Second Generation Sensitizers: Where are We and Where Should We Be Going?", *Proc. SPIE Int. Soc. Opt. Eng. Ser.*, 6:87–106, 1990.

Perrouault et al., "Sequence–Specific Artificial Photo–Induced Endonucleases Based on Triple Helix–Forming Oligonucleotides," *Nature*, 344:358–360, 1990.

Pieles and Englisch, "Psoralen Covalently Linked to Oligodeoxyribonucleotides: Synthesis, Sequence Specific Recognition of DNA and Photo–Cross–Linking to Pyrimidine Residues of DNA," *Nucleic Acids Res.*, 17(1);285–299, 1989.

Praseuth et al., "Sequence–Targeted Photosensitized Reactions in Nucleic Acids by Oligo–α–Deoxynucleotides and Oligo–β–Deoxynucleotides Covalently Linked to Proflavin," *Biochemistry*,27:3031–3038, 1988.

Praseuth et al., "Sequence–Specific Binding and Photo-crosslinking of α and β Oligodeoxynuclotides to the Major Groove of DNA via Triple–Helix Formation," *Proc. Natl. Acad. Sci. USA*, 85;1349–1353, 1988.

Takasugi et al., "Sequence–Specific Photo–Induced Cross–Linking of the Two Strands of Double–Helical DNA by a Psoralen Covalently Linked to a Triple Helix–Forming Oligonucleotide," *Proc. Natl. Acad. Sci. USA*, 88:5602–5606, 1991.

Teare, and Wollenzien, "Specificity of Site Directed Psoralen Addition to RNA," *Nucleic Acids Res.*, 17(9):3359–3372, 1989.

Vogel et al., "New Porphycene Ligands: Octaethyl–and Etioporphycene (OEPc) and EtioPc)–Tetra–and Pentacoor-dinated Zinc Complexes of OEPc," *Angew. Chem. Int. Ed. Engl.*, 32(11):1600–1604, 1993.

Wessel et al., "Porphyrins with Aromatic 26π–Electron Systems," *Agnew. Chem. Int. Ed. Eng.*, 32(8):1148–1151, 1993.

Agrawal et al., "Cellular Uptake and Anti–HIV Activity of Oligonucleotides and Their Analogs," *Gene Regulation: Biology of Antisense RNA and DNA*, 273–283, 1992.

Agrawal and Tang, "Efficient Synthesis of Oligoribonucle-otide and Its Phosphorothioate Analogue Using H–Phospho-nate Approach," *Tetrahedron Letters*, 31(52):7541–7544, 1990.

Akhtar et al., "Pharmaceutical Aspects of the Biological Stability and Membrane Transport Characteristics of Antisense Oligonucleotides," *Gene Regulation: Biology of Antisense RNA and DNA*, 133–145, 1992.

Basile et al., "Metal–Activated Hydrolytic Cleavage of DNA," *J. Am. Chem. Soc.*, 109:7550–7751, 1987.

Bradley et al., "Antisense Therapeutics," *Gene Regulation: Biology of Antisense RNA and DNA*, 285–293, 1992.

Breslow et al., "Effects of Metal Ions, Including $Mg^{2+}$ and Lanthanides, on the Cleavage of Ribonucleotides and RNA Model Compounds," *Proc. Natl. Acad. Sci. USA*, 88:4080–4083, 1991.

Browne and Bruice, "Chemistry of Phosphodiesters, DNA and Models. 2. The Hydrolysis of Bis(8–hydroxyquinoline) Phosphate in the Absence and Presence of Metal Ions," *Journal of the American Chemical Society*, 114(13):4951–4958, 1992.

Chin and Banasczyk, "Rate–Determining Complexation in Catalytic Hydrolysis of Unactivated Esters in Neutral Water," *J. Am. Chem. Soc.*, 111:2724–2726, 1989.

Chin and Banaszczyk, "Highly Efficient Hydrolytic Cleavage of Adenosine Monophosphate Resulting in a Binuclear Co(III) Complex with a Novel Doubly Bidentate $\mu^4$–Phos-phato Bridge," *J. Am. Chem. Soc.*, 111:4103–4105, 1989.

Chin et al., "Co(III) Complex Promoted Hydrolysis of Phosphate Diesters: Comparison in Reactivity of Rigid cis–Diaquotetraazacobalt(III) Complexes," *J. Am. Chem. Soc.*,111:186–190, 1989.

Chin and Zou, "Catalytic Hydrolysis of cAMP," *Can. J. Chem.*, 65:1882–1884, 1987.

Chung et al., "Synthesis and Characterization of a Reactive Binuclear Co(III) Complex. Cooperative Promotion of Phosphodiester Hydrolysis," *Tetrahedron Letters*, 31(38):5413–5416, 1990.

Cohen, Jack, S., "Chemically Modified Oligodeoxynucle-otide Analogs as Regulators of Viral and Cellular Gene Expression," *Gene Regulation: Biology of Antisense RNA and DNA*, 247–259, 1992.

Furuta et al., "Phosphate Anion Binding: Enhanced Transport of Nucleotide Monophosphates Using a Sapphyrin Carrier," *J. Am. Chem. Soc.*, 113:6677–6678, 1991.

Hanvey et al., "Antisense and Antigene Properties of Peptide Nucleic Acids," *Science*, 258:1481–1485, 1992.

Hendry and Sargeson, "Metal Ion Promoted Phosphate Ester Hydrolysis. Intramolecular Attack of Coordinated Hydroxide Ion," *J. Am. Chem. Soc.*, 111:2521–2527, 1989.

Kim and Chin, "Dimethyl Phosphate Hydrolysis at Neutral pH," *J. Am. Chem. Soc.*, 114:9792–9795, 1992.

Komiyama et al., "Unprecedentedly Fast Hydrolysis of the RNA Dinucleoside Monophosphates ApA and UpU by Rare Earth Metal Ions," *J. Chem. Soc. Chem. Commun.*, 640–641, 1992.

Merger et al., "Phosphate Ester Hydrolysis Catalyzed by Metallomicelles," *J. Am. Chem. Soc.*,109:2800–2803, 1987.

Modak et al., "Torward Chemical Ribonucleases. 2. Synthesis and Characterization of Nucleoside–Bipyridine Conjugates. Hydrolytic Cleavage of RNA by Their Copper(II) Complexes," *J. Am. Chem. Soc.*, 113:283–291, 1991.

Morrow et al., "Efficient Catalytic Cleavage of RNA by Lanthanide(III) Macrocyclic Complexes: Toward Synthetic Nucleases for in Vivo Applications,"*J. Am. Chem. Soc.*, 114:1903–1905, 1992.

Ranganathan et al., "Design of a Chemical Nuclease Model with $(Lys)_2Cu$ as the Core Motif," *Journal of the Chemical Society*, 4:337–339, 1993.

Sessler et al., "Sapphyrins: New Life for an Old Expanded Porphyrin," *Synlett*, 127–134, 1991.

Sessler et al., "Sapphyrins and Heterosapphyrins," *Tetrahedron*, 48(44):9661–9672, 1992.

Shelton and Morrow, "Catalytic Transesterification and Hydrolysis of RNA by Zinc(II) Complexes," *Inorganic Chemistry*, 30:4295–4299, 1991.

Stern et al., "Hydrolysis of RNA by Transition–Metal Complexes," *J. Am. Chem. Soc.*, 112:5357–5359, 1990.

Sumaoka et al., "Remarkably Fast Hydrolysis of 3',5'–Cyclic Adenosine Monophosphate by Cerium (III) Hydroxide Cluster," *J. Chem. Soc. Chem. Comm.*, 2 pages, 1992.

To and Neiman, "The Potential For Effective Antisense Inhibition of Retroviral Replication Mediated by Retroviral Vectors," *Gene Regulation: Biology of Antisense RNA and DNA*, 261–271, 1992.

Phillips and Wasserman, "Promise of Radiosensitizers and Radioprotectors in the Treatment of Human Cancer," *Cancer Treatment Reports*, 68(1):291–301, 1984.

Wagener and Beyrich, "Radiosensitizer–Biochemie und Tumortherapeutische Erfahrungen," *Pharmazie*, 47:815–824, 1992.

Kolasa et al., "Trivalent Lanthanide Ions Do Not Cleave RNA in DNA–RNA Hybrids," *Inorg. Chem.*, 32:3983–3984, 1993.

Schneider et al., "Catalysis of the Hydrolysis of Phosphoric Acid Diesters by Lanthanide Ions and the Influence of Ligands," *Angew. Chem. Int. Ed. Engl.*, 32(12):1716–1719, 1993.

Hayashi et al., "Site–Selective Hydrolysis of tRNA by Lanthanide Metal Complexes," *Inorg. Chem.*, 32:5899–5900, 1993.

Magda et al, "Sequence–Specific Photocleavage of DNA by an Expanded Prophyrin with Irradiation Above 700 mn," J.Am. Chem. Soc., 117:3629–3630, 1995.

Sessler et al., "Expanded Porphyrins. Receptors for Cationic, Anionic, and Neutral Substrates," in Transition Metals in Supramolecular Chemistry, NATO ASI Series, Kluwer, Amsterdam, pp. 391–408, 1994.

Casas et al., "Preparation of Hybrid DNA Cleaver–Oligonucleotide Molecules Based on a Metallotris(methylpyridiniumyl)porphyrin Motif," *Bioconjugate Chem.*, 4:366–371 (1993).

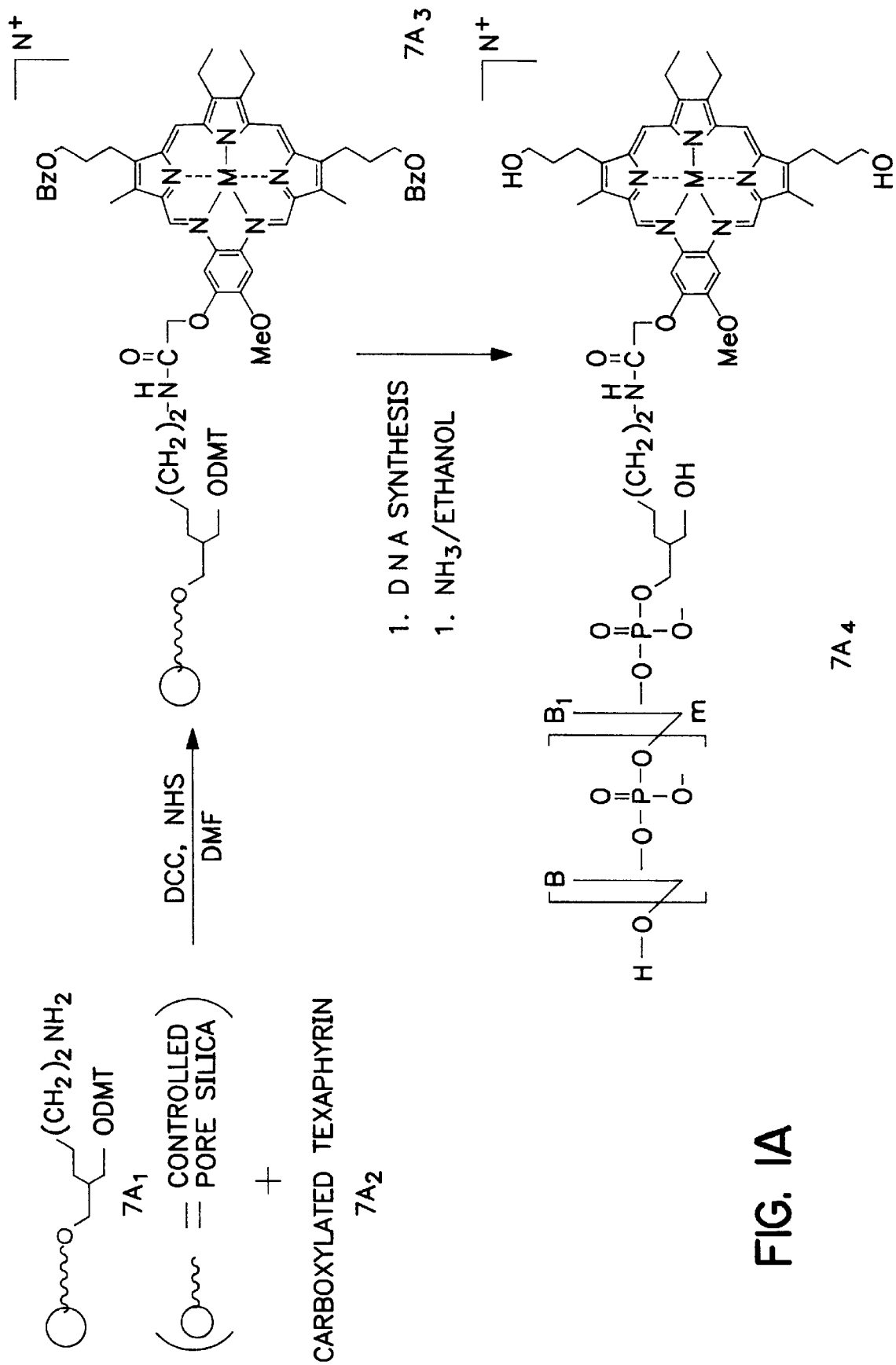
FIG. IA

PHOSPHORAMIDITE DERIVATIVES OF MACROCYCLES

This application is a continuation-in-part of U.S. application Ser. No. 08/614,638, filed Mar. 13, 1996, now U.S. Pat. No. 5,633,354, which is a continuation of U.S. application Ser. No. 08/487,722, filed Jun. 7, 1995, now U.S. Pat. No. 5,565,552, which is a continuation-in-part of U.S. application Ser. No. 08/310,501, filed Sep. 21, 1994, now U.S. Pat. No. 5,567,687. Benefit of the filing dates of said earlier filed applications are claimed under 35 U.S.C. §120.

FIELD OF THE INVENTION

The present invention relates to a method of step-wise synthesis of conjugates of oligonucleotides and macrocycles such as porphyrins and expanded porphyrins, and to phosphoramidite derivatives useful as intermediates therefor.

BACKGROUND OF THE INVENTION

Porphyrins are compounds widely distributed throughout nature consisting of four pyrroles joined in a ring structure. They comprise several varieties, differing for the most part in the sidechains present at the eight available positions on the pyrrole rings. Porphyrins combine with various metals, such as iron, copper, magnesium, and the like, to form metalloporphyrins, and with certain electrophiles to form N-substituted derivatives. Examples of naturally occurring porphyrins are found in hemoglobin (iron (II) protoporphyrin IX) and most cytochromes.

"Expanded porphyrins" are large, pyrrole-containing macrocyclic analogues of the porphyrins. Examples of these compounds are the smaragdyrins, sapphyrins, oxosapphyrins, platyrins, pentaphyrins, hexaphyrins, superphthalocyanines, rubyrins, and texaphyrins. Such molecules are of potential interest because suitably designed systems could act as versatile ligands capable of binding larger metal cations and/or stabilizing higher coordination geometries than those routinely accommodated within the normally tetradentate ca. 2.0 Å radius porphyrin core. The resulting complexes could have important application in the area of heavy metal chelation therapy, serve as contrast agents for magnetic resonance imaging (MRI) applications, act as vehicles for radioimmunological labeling work, or serve as useful photosensitizers for photodynamic therapeutic applications.

The texaphyrins have been found to be useful as MRI contrast agents, as radiation sensitizers and in photodynamic therapy (PDT), as well as having the ability to hydrolytically cleave phosphate esters, including RNA, and to photolytically cleave RNA and DNA. Texaphyrin is considered as being an aromatic benzannulene containing both 18$\pi$- and 22$\pi$-electron delocalization pathways. See, e.g., Sessler, J. L. et al., *Accounts of Chemical Research*, 1994, 27, 43. Texaphyrins and water-soluble texaphyrins and method of preparation have been described in U.S. Pat. Nos. 4,935,498; 5,252,720; 5,256,399; 5,272,142; 5,292,414; 5,457,183; 5,583,220; 5,599,923; and 5,599,928; and in International publn.s WO 94/29316 and WO 95/01996; all of which are incorporated herein by reference.

Sapphyrins and water-soluble sapphyrins and methods of preparation having been described in U.S. Pat. Nos. 5,041,078; 5,120,411; 5,159,065; 5,302,714; 5,457,195; and 5,530,123 and in International publn. WO 94/09003; all of which are incorporated herein by reference. Rubyrins are described in U.S. Pat. No. 5,410,045, incorporated herein by reference.

SUMMARY OF THE INVENTION

The present invention is directed to a method of incorporating macrocycles such as porphyrins and expanded porphyrins before, during, or after chemical synthesis of an oligomer to form a macrocycle-oligonucleotide conjugate. In one embodiment of the invention, the method is directed to the incorporation of a sapphyrin or a texaphyrin during oligomer synthesis to give a sapphyrin- or texaphyrin-oligonucleotide conjugate. The method of the invention comprises the steps of obtaining an automated or manual DNA synthesizer. Further steps include reacting derivatized oligonucleotides and a porphyrin or an expanded porphyrin, such as a sapphyrin or a texaphyrin, in a desired order to form, for example, a porphyrin-, a sapphyrin- or a texaphyrin-oligonucleotide conjugate. For example, an oligonucleotide may be formed by repeated steps of reacting nucleotides on the solid support of the DNA synthesizer. A macrocycle may be coupled in the final step to form a conjugate with a 5' linkage. Alternatively, a macrocycle may be coupled to the solid support followed by the addition of nucleotides to form a conjugate with a 3' linkage. A third possibility is the coupling of nucleotides followed by a macrocycle, such as a porphyrin, a texaphyrin or a sapphyrin, then followed by nucleotides to form a conjugate where an internal residue is the macrocycle. Another method for obtaining a macrocycle internally in the oligonucleotide sequence is to prepare the entire oligonucleotide sequence and then, as a last step, to attach or couple the macrocycle to one of the internal nucleotides, after removal of a suitable protective group on the selected nucleotide, to form a conjugate with a linkage at an internal site.

The oligonucleotide may be linked to the macrocycle in a 3' linkage, a 5' linkage, or a linkage internal to the oligonucleotide. The macrocycle may be coupled as a phosphoramidite, H-phosphonate, or phosphate triester derivative and may be coupled to the growing end of the oligonucleotide in the synthesizer either during or in the final step of synthesis.

The invention is further directed to phosphoramidite derivatives of macrocycles, such as porphyrins and expanded porphyrins, including sapphyrins and texaphyrins. The phosphoramidite derivatives are useful as intermediates in the preparation of macrocycle-oligonucleotide conjugates via, for example, the synthesis methods disclosed and described herein.

Following long-standing patent law convention, the terms "a" and "an" mean "one or more" when used in this application, including the claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A, FIG. 1B, FIG. 1C, FIG. 1D, FIG. 1E, FIG. 1F, FIG. 1G and FIG. 1H show stepwise synthesis schemes for preparing texaphyrin phosphoramidite derivatives and sapphyrin phosphoramidite derivatives and their use in the synthesis of texaphyrin metal complex-oligonucleotide conjugates and sapphyrin-oligonucleotide conjugates. FIG. 1A shows the synthesis of a texaphyrin metal complex 3'-linked oligonucleotide conjugate. FIG. 1B and FIG. 1C show an approach that results in a 5'-linked oligonucleotide conjugate. FIG. 1D shows the synthesis of a 5'-linked sapphyrin-oligonucleotide conjugate. FIG. 1E shows the synthesis of a precursor sapphyrin that may be linked to two oligonucleotides. FIG. 1F and FIG. 1G show the synthesis of a sapphyrin oligonucleotide conjugate via the H-phosphonate method. FIG. 1H shows a synthesis through a sapphyrin phosphoramidite derivative that gives a 5'-linked sapphyrin-oligonucleotide conjugate. Example 1 provides the details of these stepwise synthesis schemes. In FIGS. 1A–1C, M is H, a divalent metal cation or a trivalent metal cation; "An" and "Bz" are protecting groups; m is an integer of 1 to 100 or greater; n is zero or an integer less than or equal to 10; and $N^+$ will typically be an integer less than or equal to 5. In the context of the basic macrocycle with a divalent or trivalent metal cation, $N^+$ is 1 or 2; however, the complexes may have one or more additional ligands providing charge neutralization and/or coordinative saturation to the metal ion. In FIGS. 1D–1H, "DMT" indicates a protecting group, m is an integer of 1 to 100 or greater, and n is zero or an integer less than or equal to 10.

DETAILED DESCRIPTION OF THE PREFERRED EMBODIMENTS

Figure 1B:
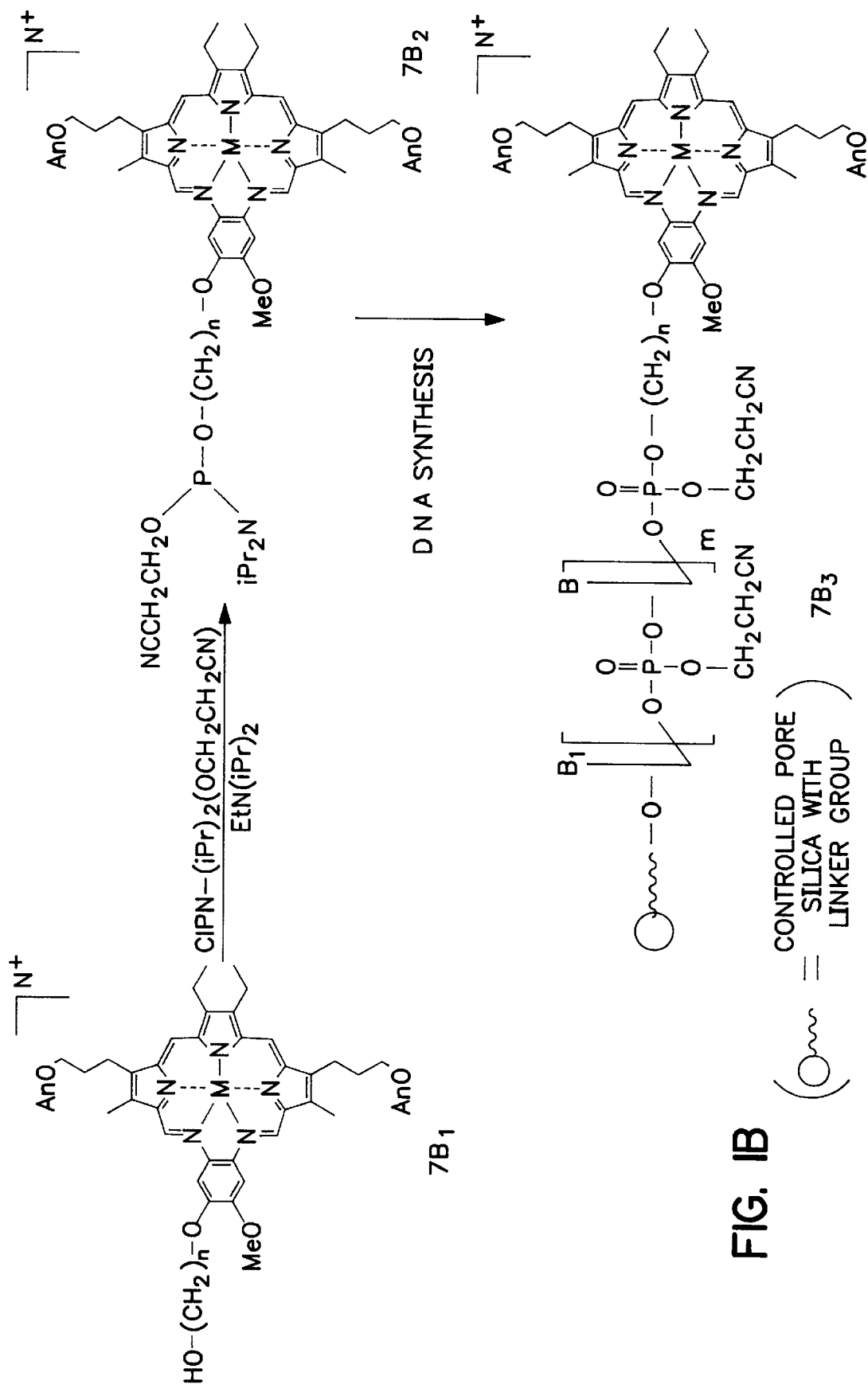
Figure 1C:
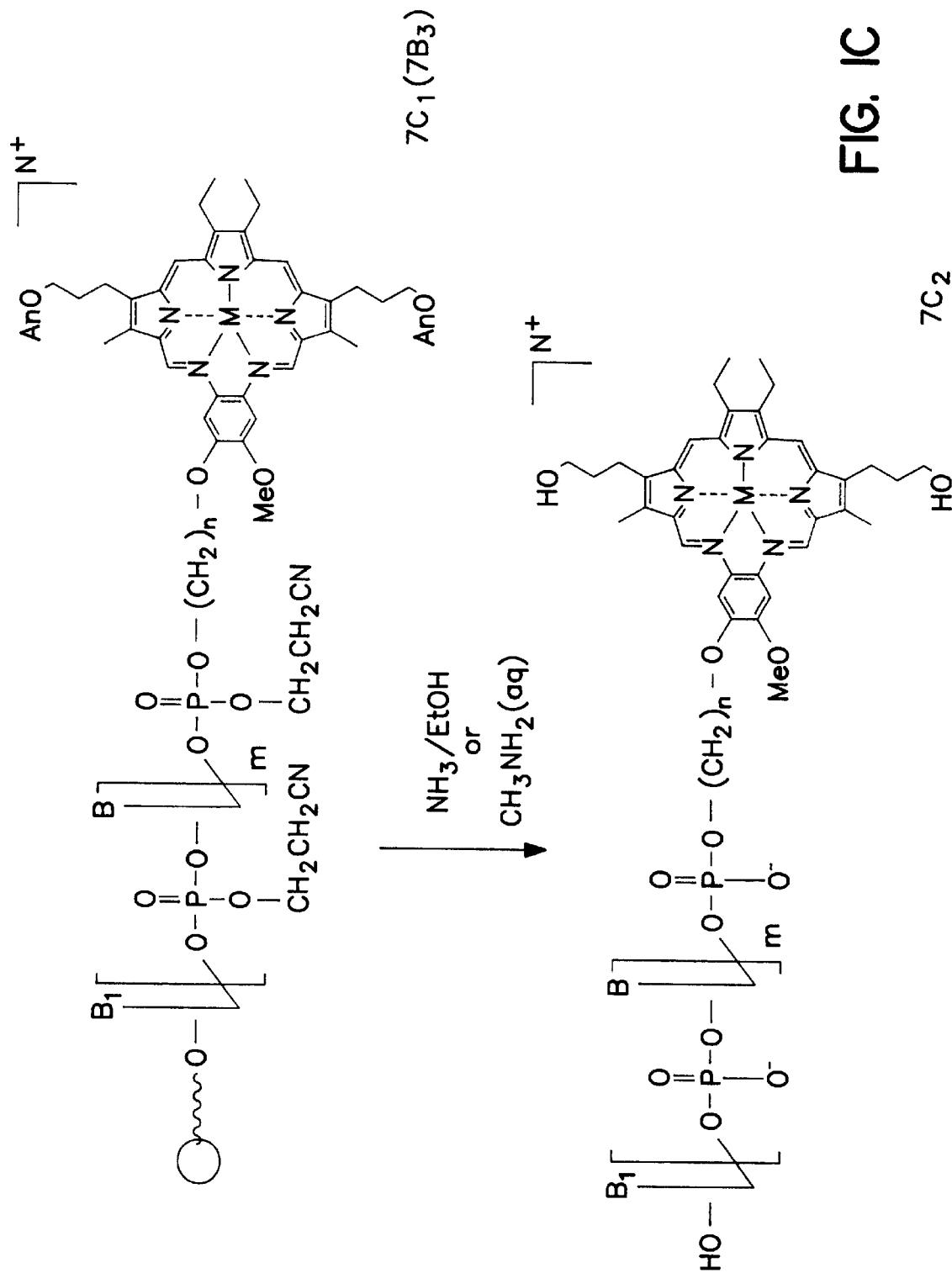

The present invention provides synthetic procedures in which a macrocycle such as a porphyrin, an expanded porphyrin, and in particular a texaphyrin or a sapphyrin, is inserted, via a phosphoramidite derivative of the macrocycle, directly into a nucleic acid synthesis scheme, preferably on a solid support. Texaphyrin and sapphyrin macrocycles were not known to be stable under the basic conditions employed in the synthesis of oligonucleotides. For example, until the results presented herein were obtained, it was thought that texaphyrin, being a Schiff base, may be unstable to the basic conditions employed during oligonucleotide synthesis, specifically during the ammonia and ethanol, or methylamine and ammonium hydroxide, cleavage and deprotection steps. It was also thought that the meso positions of sapphyrin would be unstable to the same basic conditions. Therefore, the stepwise synthesis of texaphyrin- and sapphyrin-oligonucleotide conjugates presented herein was a surprising and unexpected result. The synthesis of sapphyrin-nucleobase conjugates is described in U.S. Pat. No. 5,457,195 and International publn. WO 94/09003, incorporated by reference herein.

It is contemplated that the stepwise synthesis provided herein may be performed manually or may be automated, and may be in a solution-phase or on a solid support. Solid support synthesis may be accomplished using an automated or a manual nucleic acid synthesizer. Common solid supports are CPG (control pore glass) and CPS (control pore silica). Other possible solid supports include polystyrene, polyamide/Kieselguhr, and cellulose paper. A preferred embodiment of this method is automated synthesis on a solid support.

Attachment of a macrocycle to an oligonucleotide during stepwise synthesis obviates the need for a postmodification protocol and a second purification of the product. This results in an improved yield and greatly facilitates scale-up.

Oligomeric DNA, up to ca 100 residues in length, can be prepared on a commercial synthesizer, such as for example Applied Biosystems Inc. model 392. Most commercial synthesizers employ phosphoramidite chemistry. In brief, DNA is synthesized from the 3' to the 5' direction through the sequential addition of highly reactive phosphorus(III) reagents called phosphoramidites. The initial 3' residue is covalently attached to a controlled porosity silica solid support, which greatly facilitates manipulation of the polymer. After each residue is coupled to the growing polymer chain, the phosphorus(III) is oxidized to the more stable phosphorus(V) state by a short treatment with iodine solution. Unreacted residues are capped with acetic anhydride, the 5'-protective group is removed with weak acid, and the cycle may be repeated to add another residue. The full-length polymer is released from the solid support, with concomitant removal of remaining protective groups, by exposure to base. A common protocol uses saturated ethanolic ammonia; another uses methylamine and conc. ammonium hydroxide.

The finding that lanthanide(III) metal complexes of texaphyrins, notably DyT2B2 (cpd. $1_A$, M=Dy) and EuT2B1 (cpd. $1_B$, M=Eu), are stable to treatment with ethanolic ammonia for 24 h at ambient temperature first indicated that it is possible to derivatize oligomers with lanthanide(III) texaphyrin complexes during stepwise synthesis to produce texaphyrin-oligonucleotide conjugates, such as for example cpd. $1_c$.

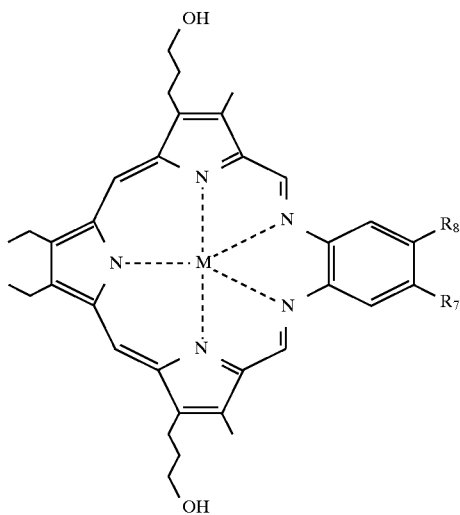

$1_A$ $R_7 = R_8 = OCH_2CH_2CH_2OH$
$1_B$ $R_7 = H$, $R_8 = OCH_2CO_2H$
$1_C$ $R_7 = H$, $R_8 = OCH_2CO$-DNA

A porphyrin or an expanded porphyrin, such as a texaphyrin or metal complex thereof or a sapphyrin molecule, may be inserted into the synthesis scheme of an oligonucleotide in a variety of ways. Possible linkages include amide, phosphate, thioether, amino, and ether linkages. An amide linkage represents the reaction of an activated carboxylic acid derivative of a macrocycle (such as cpd. $1_B$) and an amino linker attached to an oligonucleotide. Activation may be achieved in solution phase or on a solid support using dicyclohexylcarbodiimide (DCC) and N-hydroxysuccinimide (NHS), 1-ethyl-3-(3-dimethylaminopropyl)carbodiimide HCl (EDC), or activated esters of NHS, nitrophenyl, pentachlorophenyl, acid anhydride, or sulfonyl chloride. In addition, for the solid support reaction, activation may be in the form of an acid chloride. A phosphate linkage results from the reaction of an activated phosphate derivative of a macrocycle and the 5' hydroxyl group on an oligonucleotide. The activated phosphate may be a phosphoramidite, an H-phosphonate, a triester, or a diester.

The terms "porphyrin-oligonucleotide conjugate", "expanded porphyrin-oligonucleotide conjugate", "sapphyrin-oligonucleotide conjugate" and "texaphyrin-oligonucleotide conjugate" mean that a nucleotide or an oligonucleotide is attached to the porphyrin, expanded porphyrin, sapphyrin or texaphyrin, respectively, in a 5' or a 3' linkage, or in both types of linkages to allow the macrocycle to be an internal residue in the conjugate. It can also refer to a porphyrin, an expanded porphyrin, a sapphyrin or a texaphyrin, respectively, that is linked to an internal base of the nucleotide or oligonucleotide. The nucleotide or oligonucleotide may be attached either directly to the macrocycle or to the macrocycle via a linker or a couple of variable length.

It is understood that the terms "nucleotide", "polynucleotide" and "oligonucleotide", as used herein and in the appended claims, refer to both naturally-occurring and synthetic nucleotides, poly- and oligonucleotides and to analogs and derivatives thereof such as methylphosphonates, phosphotriesters, phosphorothioates and phosphoramidates and the like. Deoxyribonucleotides, deoxyribonucleotide analogs and ribonucleotide analogs are contemplated as being useful in the present invention.

The nucleotides or oligonucleotides may be derivatized at the bases, the sugars, the ends of the chains, or at the phosphate groups of the backbone to promote in vivo stability. Modifications of the phosphate groups are preferred in one embodiment since phosphate linkages are sensitive to nuclease activity. Presently preferred oligonucleotide derivatives are the methylphosphonates, phosphotriesters, phosphorothioates, and phosphoramidates. Additionally, the phosphate linkages may be completely substituted with non-phosphate linkages such as amide linkages. Appendages to the ends of the oligonucleotide chains also provide exonuclease resistance. Sugar modifications may include groups, such as halo, alkyl, alkenyl or alkoxy groups, attached to an oxygen of a ribose moiety in a ribonucleotide. In a preferred embodiment, the group will be attached to the 2' oxygen of the ribose. In particular, halogen moieties such as fluoro may be used. The alkoxy group may be methoxy, ethoxy, propoxy or methoxyethoxy. The alkenyl group is preferably allyl. The alkyl group is preferably a methyl group and the methyl group is attached to the 2' oxygen of the ribose. Other alkyl groups may be ethyl or propyl.

Representatives of texaphyrins which may be activated and attached to nucleotides following the present invention are included within the following structure I:

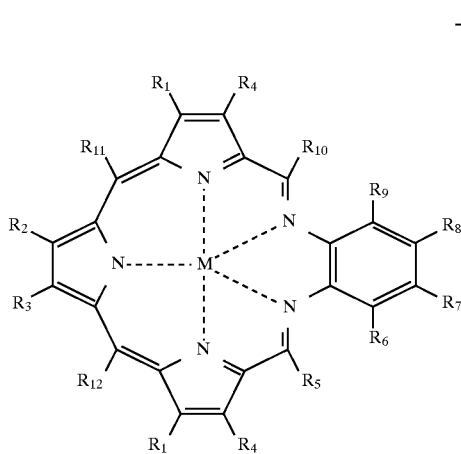

wherein, M is H, a divalent metal cation or a trivalent metal cation; $R_1$–$R_4$, $R_7$ and $R_8$ are independently hydrogen, halide, hydroxyl, alkyl, aryl, haloalkyl, nitro, formyl, acyl, hydroxyalkyl, oxyalkyl, oxyhydroxyalkyl, saccharide, carboxy, carboxyalkyl, carboxyamide, carboxyamidealkyl, aminoalkyl, sulfonatoalkyl, amidealkyl, aryl, or the group —$(CH_2)_t$—O—W where W is hydrogen or a protecting group and t is an integer less than or equal to 10; $R_6$ and $R_9$ are independently selected from the groups of $R_1$–$R_4$, $R_7$ and $R_8$, with the proviso that the halide is other than iodide and the haloalkyl is other than iodoalkyl; $R_5$ and $R_{10}$–$R_{12}$ are independently hydrogen, alkyl, aryl, hydroxyalkyl, oxyalkyl, oxyhydroxyalkyl, carboxyalkyl, or carboxyamidealkyl; and Z will typically be an integer less than or equal to 5. In the context of the basic macrocycle with a divalent or trivalent metal cation, $N^+$ is 1 or 2; however, the complexes may have one or more additional ligands providing charge neutralization and/or coordinative saturation to the metal ion.

Additional texaphyrins are disclosed in the patents previously incorporated herein by reference. Such texaphyrins are also useful in the present invention.

Sapphyrins which may be activated and attached to nucleotides following the present invention are disclosed in the patents and publications previously incorporated herein by reference. Representatives of such sapphyrins are included within the following structure III:

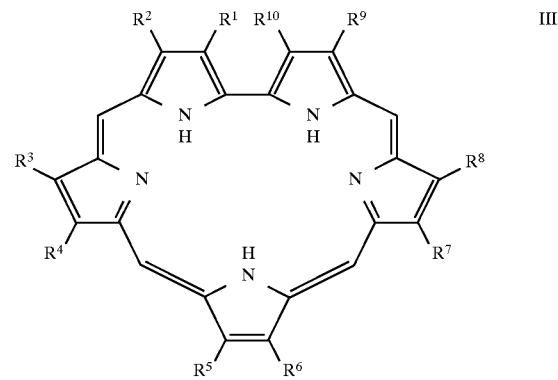

wherein, each of $R^1$–$R^{10}$ is independently selected from hydrogen, alkyl, alkenyl, alkynyl, halo, haloalkyl, hydroxyalkyl, glycol, polyglycol, thiol, alkyl thiol, aminoalkyl, carboxyalkyl, alkoxyalkyl, aryloxyalkyl, alkyloxycarbonyl, aryloxycarbonyl, CHO—, an ether group, a ketone group, carboxyl, phosphate, phosphonate, sulfate, phosphate-substituted alkyl, phosphonate-substituted alkyl, sulfate-substituted alkyl, phosphoramidityl, alkylphosphoramidityl, alkoxyphosphoramidityl, the group —$(CH_2)_t$—O—W where W is hydrogen or a protecting group and t is an integer less than or equal to 10, or the group —$(CH_2)_x$—A—$(CH_2)_y$—B, where A is $CH_2$, O, S, NH or $NR^{11}$, where $R^{11}$ is alkyl, alkenyl, alkynyl, halo haloalkyl, hydroxyalkyl, glycol, polyglycol, thiol, alkyl thiol, aminoalkyl, carboxyalkyl, alkoxyalkyl, aryloxyalkyl, alkyloxycarbonyl, aryloxycarbonyl, CHO—, an ether group, a ketone group, carboxyl, phosphate, phosphonate, sulfate, phosphate-substituted alkyl, phosphonate-substituted alkyl, sulfate-substituted alkyl, COO, CONH, CSNH, or $CONR^{11}$; B is selected from the values of A, aryl, silyl, siloxy, aminoaryl, amino, amidoaryl, sugar, sugar derivative, polysaccharide, metal chelating group, alkylating agent, steroid, steroid derivative, amino acid, peptide, or polypeptide; and each of x and y is independently an integer of less than or equal to 10 or are zero.

Suitable protecting groups W include, but are not limited to, benzoyl ("Bz"), dimethoxytrityl ("DMT"), anisoyl ("An") and the like. Such protecting groups are well known to those skilled in the art.

Phosphoramidite derivatives of the texaphyrins and the sapphyrins are formed when a texaphyrin or a sapphyrin has been activated such that a phosphoramidityl, an alkylphosphoramidityl, or an alkoxyphosphoramidityl group becomes one of the R appendages. With the porphyrins, the phosphoramidityl, alkylphosphoramidityl, or alkoxyphosphoramidityl group will be present as a sidechain or as part of a sidechain present at one of the eight available positions on the pyrrole rings of the porphyrin or at one of the meso positions on the porphyrin ring itself. The phosphoramidityl, alkylphosphoramidityl, or alkoxyphosphoramidityl group may be attached directly to the macrocycle, by a carbon-carbon, carbon-amino, carbon-oxygen or other suitable bond; or the group may be attached via a linker, such as an alkyl, alkoxy or alkylamino group having one to about ten or more carbon atoms.

An alkylphosphoramidityl group will have from one to ten carbon atoms in the alkyl portion, preferably from one to six, more preferably from three to six carbons. An alkoxyphosphoramidityl group will have from one to ten carbon atoms in the alkoxy portion, preferably from one to six, more preferably from three to six carbons.

The following examples are included to demonstrate presently preferred embodiments of the invention. However, those of skill in the art should, in light of the present disclosure, appreciate that many changes can be made in the specific embodiments that are disclosed and still obtain a like or similar result without departing from the spirit and scope of the invention.

EXAMPLE 1

Stepwise Synthesis of Texaphyrin- and Sapphyrin-Oligonucleotide Conjugates

This example discusses four representative synthetic schemes.

In the approach depicted in FIG. 1A, a metallated texaphyrin or texaphyrin-metal complex $7A_2$ is attached to a solid support $7A_1$ via a six-carbon amine linker. This amide-forming coupling reaction is currently employed to attach the complex post-synthetically. It is important to note that texaphyrin hydroxyl groups are protected as an ester on $7A_3$ for stepwise synthesis. These protecting groups are labile to the ethanolic ammonia treatment. Such a metallated texaphyrin-derivatized support may be used for stepwise synthesis, and upon cleavage and deprotection, results in a 3'-linked metallated texaphyrin-DNA conjugate $7A_4$. The amide-forming reaction may also occur at the conclusion of DNA synthesis before deprotection and cleavage from the solid support.

As depicted in FIG. 1B, a phosphoramidite derivative of a texaphyrin-metal complex $7B_2$ is prepared by reaction of the monoalcohol $7B_1$ with phosphitylating agent and diisopropylethylamine. The hydroxyl groups are again protected as the ester for this synthesis. The resulting phosphoramidite is coupled on the synthesizer as the final residue to form $7B_3$. In this approach, deprotection results in a 5'-linked texaphyrin metal complex-DNA conjugate $7C_2$. This texaphyrin-conjugate has no amide bonds in the linker.

A texaphyrin-DNA conjugate having the texaphyrin in an internal linkage to the oligonucleotide may be synthesized using this stepwise approach. A dihydroxytexaphyrin is treated with dimethoxytrityl chloride in the presence of dimethylaminopyridine and pyridine. The resulting monoprotected texaphyrin is treated with phosphitylating agent and diisopropylethylamine to produce a monoprotected phosphoramidite. This product is coupled to a growing oligonucleotide during synthesis in place of a nucleotide residue to insert a texaphyrin in an internal linkage. The monoconjugate may then be further coupled to nucleotides to produce a texaphyrin-DNA conjugate having the texaphyrin in an internal linkage to the oligonucleotide. Additionally, phosphonate or phosphodiester derivatives of texaphyrin may be utilized to form similar internal, 3', or 5' linkages by the phosphonate or triester methods, respectively.

Oligonucleotide analog-texaphyrin conjugates may be prepared in a similar manner as herein described. In particular, phosphorothioates, 2'-O-methylated ribonucleotides, or other nucleic acid analogs such as methyl phosphonate derivatives are preferred due to the enhanced stability these derivatives provide towards nucleases in vivo.

Other macrocycles may be coupled to oligomers to form macrocycle-nucleic acid conjugates in a similar manner. For example, sapphyrin-oligonucleotide conjugates have been made using a direct coupling amide linkage method or by incorporation during oligonucleotide synthesis forming a 5' linkage via the H-phosphonate method, or by conversion to a phosphoramidite-sapphyrin derivative that is then coupled to the oligonucleotide chain. Porphyrin-oligonucleotide conjugates have been made via the porphyrin-phosphoramidite intermediate, as well.

Figure 1D:
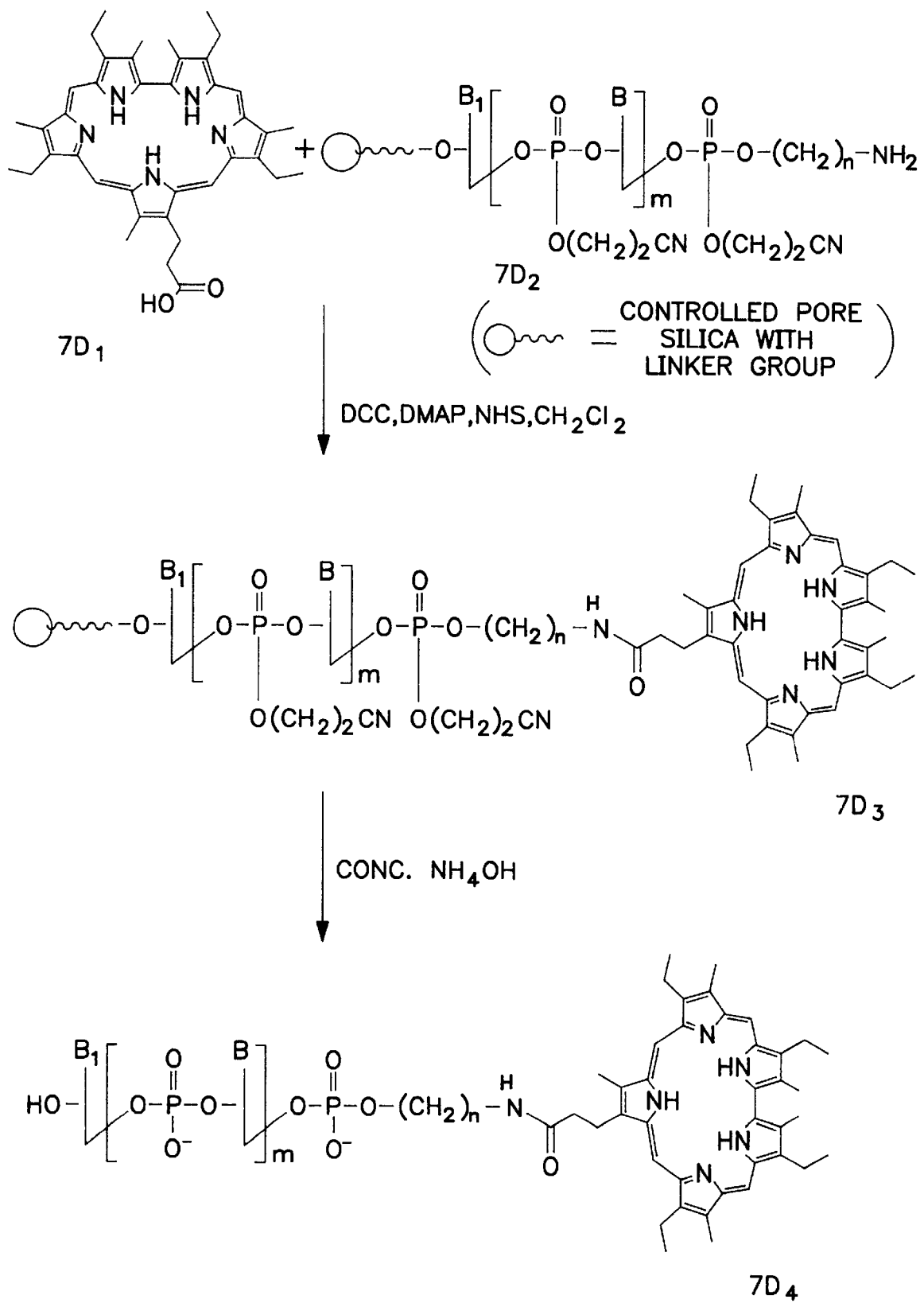

Direct coupling method (amide linkage): Sapphyrin-oligonucleotide conjugates with an amide linkage were formed on a solid support (FIG. 1D). Specifically, sapphyrin monoacid $7D_1$ (6.8 mg, 0.011 mmol, 50 eq) was dissolved in 2 mL of methylene chloride in a 4 mL glass vial with a small stirbar followed by cooling to 0° C. with an ice bath.

Dicyclohexylcarbodiimide (4.5 mg, 0.022 mmol, 100 eq), dimethylaminopyridine (0.001 mg, catalytic amount), and N-hydroxysuccinimide (2.5 mg, 0.022 eq, 100 eq) were added to the solution which was then stirred for 30 min. Protected amino-derivatized oligonucleotide attached to CPG solid support ($7D_2$ 2.5 mg, 0.108 μMol, 1 eq) was added to the solution, which was stirred overnight at room temperature. The solution was filtered, and the conjugate attached to the CPG ($7D_3$) was washed once with methylene chloride and twice with methanol. The green solids were then suspended in conc. ammonium hydroxide for 4 h at room temperature, after which the green solution was filtered and evaporated to afford the crude sapphyrin-oligonucleotide conjugate $7D_4$. The conjugate $7D_4$ could be purified by fplc on a $C_{18}$ column using acetonitrile/100 mM triethylammonium acetate, pH 7.0.

This method is similar to that described to form texaphyrin-oligonucleotide conjugates. The coupling step in this case was done on a solid support although it may be done in solution. This procedure attaches sapphyrin to the 5' end of the oligonucleotide and could be modified to link macrocycles to the 3' end, or internal to an oligonucleotide.

Figure 1E:
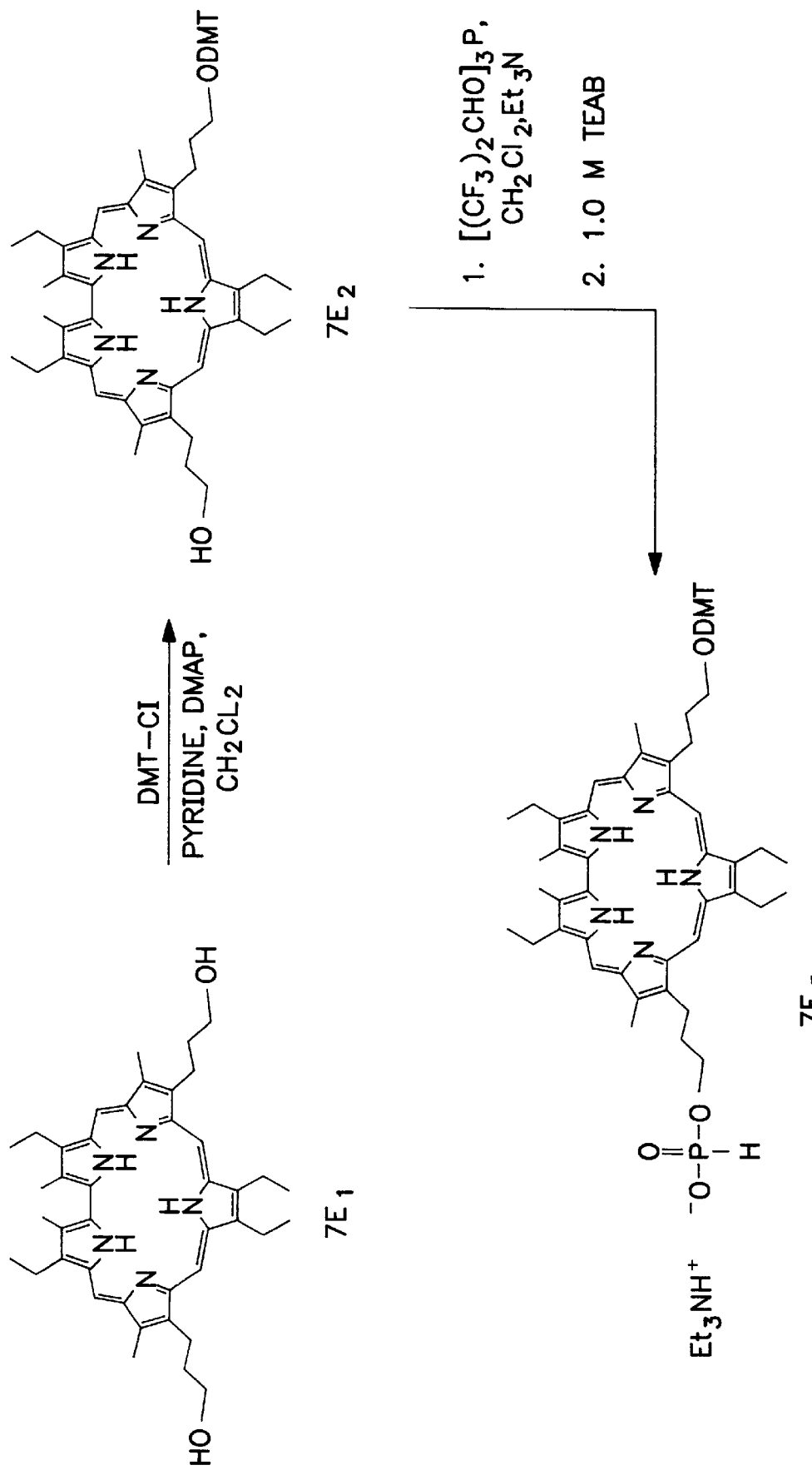
Figure 1F:
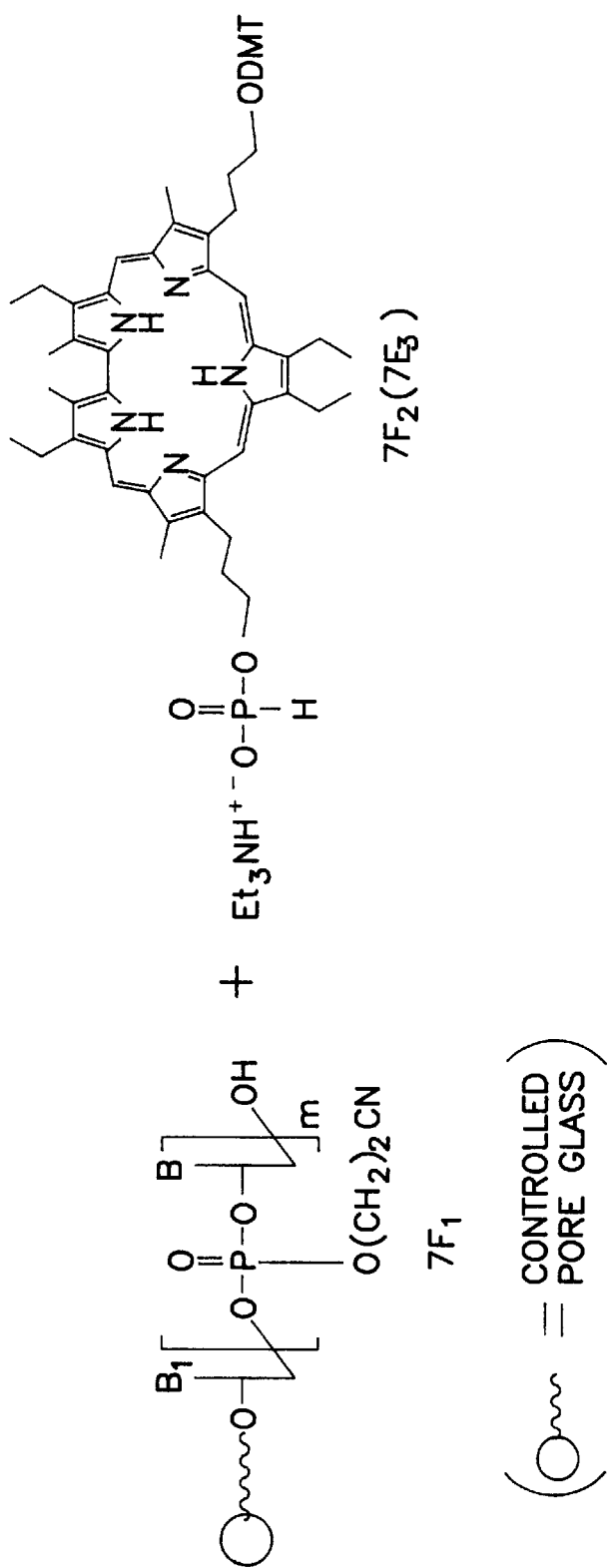
Figure 1F:
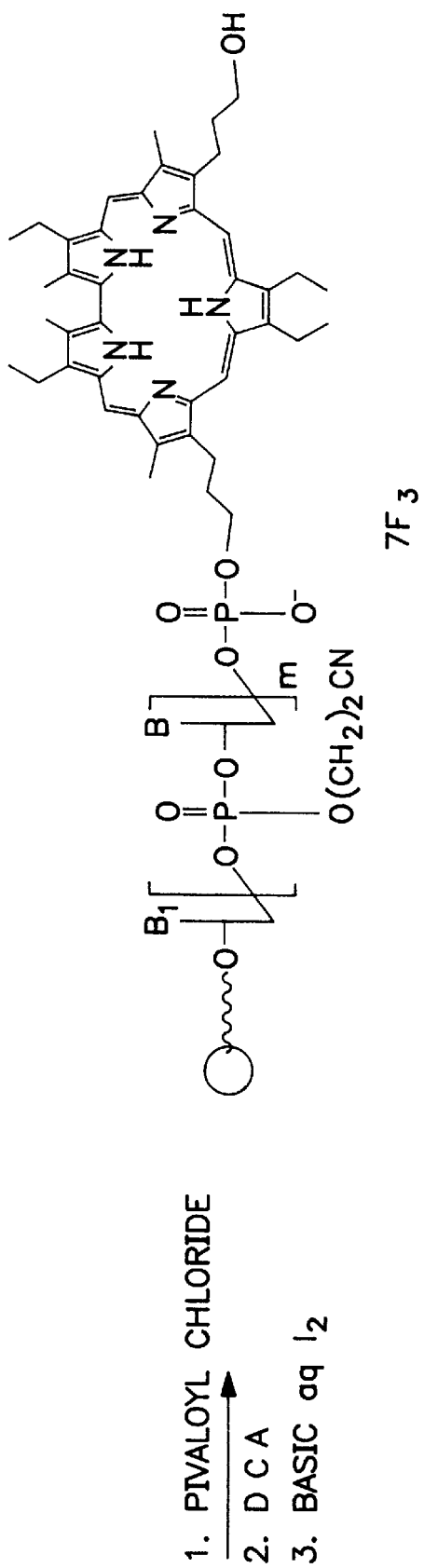
Figure 1G:
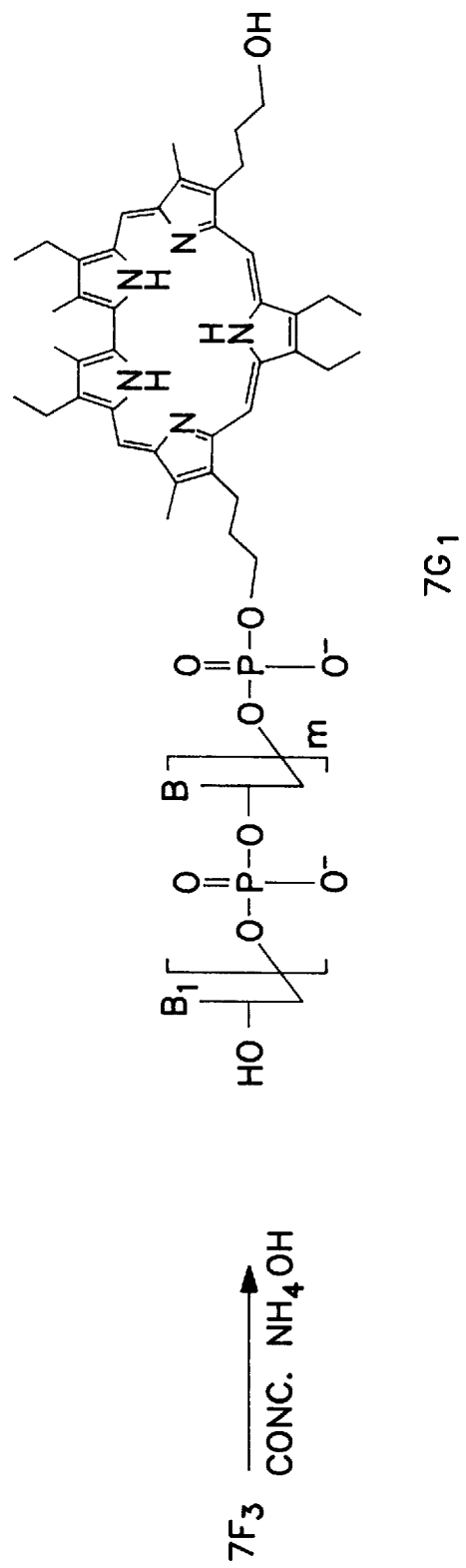

Incorporation during oligonucleotide synthesis (phosphate linkage): The monoprotected sapphyrin H-phosphonate $7F_2$ ($7E_3$) was synthesized for incorporation during oligonucleotide synthesis (FIG. 1E). A sapphyrin-conjugate $7G_1$ was synthesized in a solid-phase manual oligonucleotide synthesizer via the H-phosphonate method (FIG. 1F and FIG. 1G). The oligonucleotide was assembled on a solid support such as controlled pore glass (CPG) by a cycle of steps. The 5' end of the growing oligonucleotide was deprotected, the reaction phase was neutralized, and the activated monoprotected nucleotide H-phosphonate was coupled at the 5' end of the oligonucleotide. Derivatized sapphyrin $7F_2$ ($7E_3$) was incorporated at the 5' end of the oligonucleotide $7F_1$ during the last step of the synthesis in place of a nucleotide (FIG. 1F).

Specifically, the desired oligonucleotide was synthesized on a CPG solid support on a 0.2 μM scale. The derivatized sapphyrin $7F_2$ ($7E_3$) was attached to the oligonucleotide $7F_1$ on a manual oligonucleotide synthesizer (Cruachem PS 150 DNA Synthesizer, Sterling, Va.). The synthesis was run under argon (5 psi). Syringes were oven-dried and kept in a desiccator until use. The following sequence was used for coupling:

1. Wash—acetonitrile—2 min.
2. Deblock—3% dichloroacetic acid in methylene chloride—3 min.
3. Wash—acetonitrile—2 min.
4. Wash—acetonitrile/pyridine (1:1)—2 min.
5. Couple—4 mM derivatized sapphyrin $7F_2$ ($7E_3$) (1 eq) in methylene chloride and 65 mM pivaloyl chloride in acetonitrile/methylene chloride (1:1)—30 μL solution alternating for 1.5 min.
6. Wait—15 min.
7. Wash—acetonitrile, acetonitrile/pyridine (1:1), acetonitrile—2 min, 1 min, 2 min.
8. Deprotect—3% dichloroacetic acid in methylene chloride—3 min.
9. Wash—acetonitrile, acetonitrile/pyridine (1:1)—2 min, 2 min.
10. Oxidize—0.1M iodine in water/pyridine/N-methylimidazole/THF (5/4/1/90), 0.1M iodine in water/triethylamine/THF (5/5/90)—2 min, 2 min.
11. Wash—acetonitrile/pyridine (1:1), acetonitrile, methanol—2 min, 1 min, 2 min.

The conjugate $7F_3$ attached to CPG was added to 2 mL conc. ammonium hydroxide for 4 h. The solution was filtered and the filtrate was evaporated to afford crude sapphyrin-oligonucleotide conjugate $7G_1$ which could be purified by fplc on a $C_{18}$ column using acetonitrile/100 mM triethylammonium acetate pH 7.0.

This method may be used to synthesize any type or length of oligonucleotide with macrocycle modifications at the 5' end or in the interior of the oligonucleotide. Additionally, the oligonucleotide could be modified with multiple macrocycles.

Figure 1H:
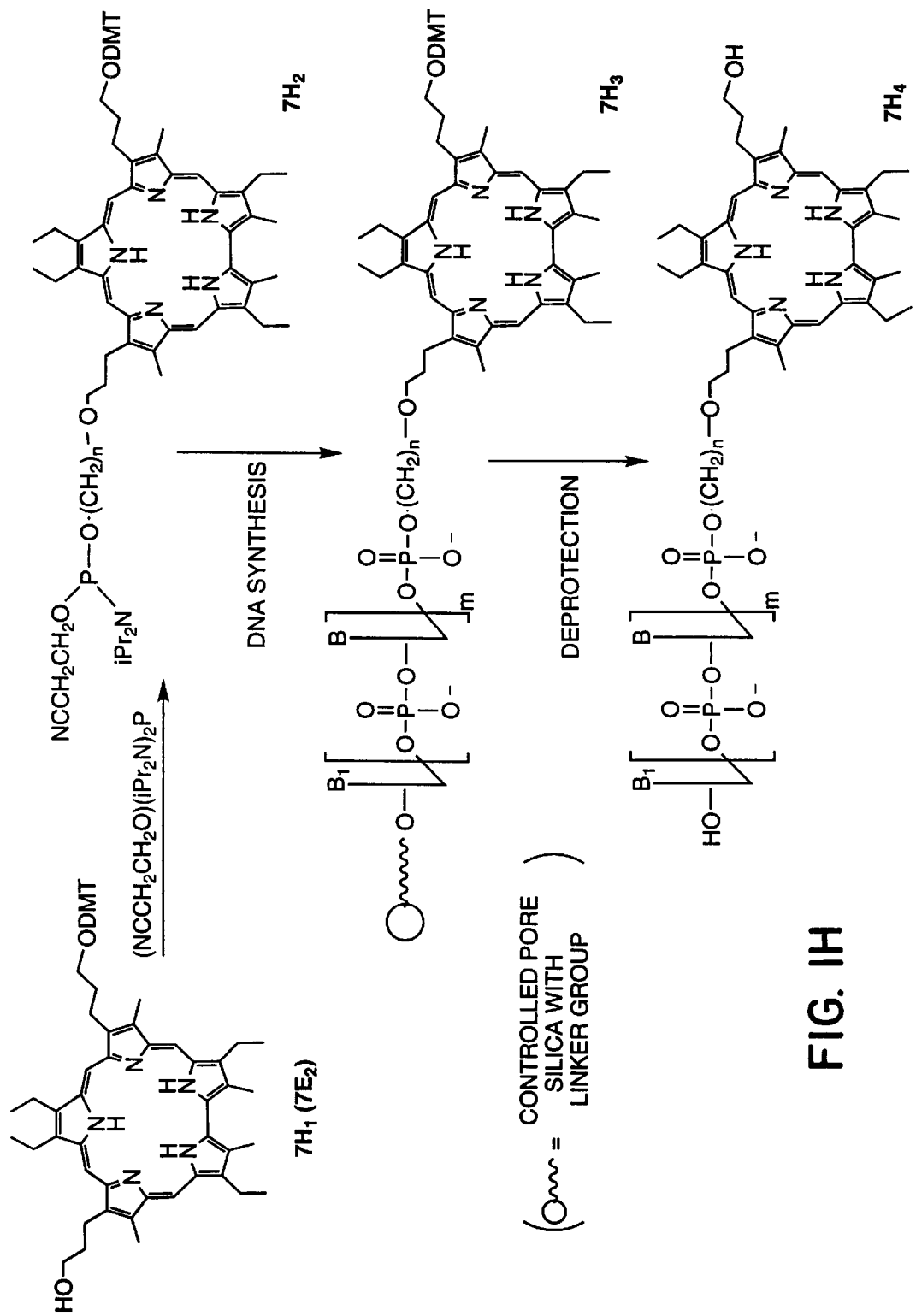

Via phosphoramidite derivative intermediate. As shown in FIG. 1H, a mono-phosphoramidite derivative of a sapphyrin $7H_2$ (prepared by reaction of a phosphitylating agent and a dihydroxy sapphyrin $7H_1$ ($7E_2$) where one of the hydroxyl groups has been protected) is coupled on the synthesizer as the final residue to form $7H_3$, after which deprotection and cleavage of the oligonucleotide conjugate from the synthesizer solid support gives the sapphyrin-oligonucleotide conjugate $7H_4$.

A further method for the synthesis of macrocycle-oligonucleotide conjugates is to incorporate nucleotides enzymatically. A variety of DNA and RNA polymerases may be used; however, the Klenow fragment of DNA polymerase I from E. coli and terminal deoxynucleotidyl transferase are preferred. Goodchild, J. (1990) provides a general discussion of the enzymatic synthesis of oligonucleotides and is incorporated by reference herein.

All of the above procedures may be followed to prepare phosphoramidite derivatives of porphyrins and porphyrin-oligonucleotide conjugates.

EXAMPLE 2

Preparation of a Texaphyrin Phosphoramidite

A texaphyrin phosphoramidite compound for use in coupling to a nucleotide according to the methods described herein was prepared as follows.

1,2-Dinitro-4-hydroxy-5-methoxybenzene. Dinitroveratrole (5 g, 0.0219 mol) was dissolved in glacial acetic acid (50 mL), and concentrated HBr (48% w/w in water, 165 mL) was added all at once at room temperature (RT). The reaction temperature was elevated to 110° C., and the system was stirred for 6 h. After cooling to RT, ice-water (150 mL) was added and a mixture of starting material and target was extracted from the aqueous phase using chloroform (2×400 mL). Target material was extracted from the chloroform layer using 2N sodium hydroxide solution (600 mL). The basic aqueous phase was washed with chloroform (2×200 mL) to remove remaining traces of starting material. The organic layers from the basic extractions were combined and dried over anhydrous magnesium sulfate. Removal of solvents under reduced pressure resulted in recovered starting material as a bright crystalline solid (2.35 g). The basic aqueous extract was acidified to pH<1 using conc. HCl (37 mL) and extracted with ethyl acetate (2×250 mL). The organic extracts were combined and dried over anhydrous magnesium sulfate. Solvents were removed under reduced pressure to yield the title compound as a yellow, powdery solid (1.82 g).

1,2-Dinitro-4-(1-hydroxyhexyl)oxy-5-methoxybenzene. To a solution of the methoxybenzene prepared above (270 mg, 1.259 mmol) in acetonitrile (40 mL) was added 6-bromo-1-hexanol (330 μL, 2.519 mmol), followed by sodium iodide (190 mg, 1.259 mmol) and potassium carbonate (697 mg, 5.045 mmol). The reaction was heated at 70° C. under a nitrogen atmosphere. After 5 days, the reaction mixture was cooled to 0° C. and filtered through a fine sintered glass funnel. Solvents were removed under reduced pressure and the resulting solid was dissolved in isopropyl alcohol (2 mL). The target product was precipitated by the addition of hexane (20 mL) to the rapidly stirred solution. The solid was filtered, washed with hexane and dried under reduced pressure to yield the crude target as a bright yellow solid (344 mg). Purification by short-bed silica gel chromatography using methylene chloride as the mobile phase resulted in the isolation of the product as a pale yellow crystalline solid (274 mg, 69%).

4-(1-Hydroxyhexyl)oxy-5-methoxy-1,2-phenylenediamine. 1,2-Dinitro-4-(1-hydroxyhexyl)oxy-5-methoxybenzene (300 mg, 0.9546 mmol) was dissolved in methanol (30 mL). Conc. HCl (1 mL) was added, followed by palladium catalyst (10% on activated carbon, 90 mg). The reaction was shaken under a hydrogen atmosphere at 45 psi. After 5 h, when the uptake of hydrogen was complete, the catalyst was removed by filtration over celite. Solvent was removed under reduced pressure to yield the target compound as the dihydrochloride salt (305 mg, 98%).

4,5,9,24-Tetraethyl-16(1-hydroxyhexyl)oxy-17-methoxy-10,23-dimethyl-pentaazapentacyclo[20.2.1.1$^{3,6}$.1$^{8,11}$.0$^{14,19}$]heptacosa-1,3,5,7,9,11(27),12,14,16,18,20,22(25),23-tridecaene. To a solution of the above phenylenediamine.2HCl (485 mg, 1.4821 mmol) in methanol (240 mL) was added solid 2,5-bis[5-formyl-3-ethyl-4-methylpyrrol-2-yl)methyl]-3,4-diethylpyrrole in one go, under a nitrogen atmosphere. After heating at 75° C. for 2 h, the reaction was allowed to cool to RT. charcoal (330 mg) was added to the solution and the system was stirred for 15 min. The charcoal was removed by filtration over celite, and the solvent was removed under reduced pressure. The target compound was isolated as the dihydrochloride salt in the form of an orange glass (900 mg, 85%).

Dysprosium complex of 4,5,9,24-tetraethyl-16(1-hydroxyhexyl)oxy-17-methoxy-10,23-dimethyl-pentaazapentacyclo[20.2.1.1$^{3,6}$.1$^{8,11}$.0$^{14,19}$]heptacosa-1,3,5,7,9,11(27),12,14,16,18,20,22(25),23-tridecaene, cpd. $2_A$. To a solution of the tridecaene prepared above (130 mg, 0.1824 mmol) in methanol (30 mL) was added dysprosium nitrate pentahydrate (120 mg, 0.2736 mmol), followed by triethylamine (260 µL, 1.834 mmol). The reaction was heated under gentle reflux open to the air. After 2.5 h, the reaction was allowed to cool to RT and was filtered through a pad of celite. Solvent was removed under reduced pressure and the resulting crude complex was triturated in acetone (30 mL) for 10 min. The solid was isolated by suction filtration and dried under reduced pressure. To remove unbound dysprosium metal ion, the complex was dissolved in a mixture of methanol/water (9:1, 15 mL) and gently agitated with zeolite (SAY-54, 600 mg), which had been previously rinsed with dilute HCl and deionized water. After 1.5 h, the zeolite was removed by filtration and the process was repeated using fresh zeolite. After removal of the zeolite, n-butyl alcohol (10 mL) was added to the system to prevent bumping during solvent removal. Solvents were removed under reduced pressure to yield the target compound $2_A$ as the dinitrate salt in the form of a deep green solid (97 mg, 58%). MS (FABLR) M—$HNO_3$—$NO_3$ 796.

Dysprosium complex of 2-cyanoethyl-N,N-diisopropyl-6-(4,5,9,24-tetraethyl-17-methoxy-10,23-dimethyl-pentaazapentacyclo[20.2.1.1$^{3,6}$.1$^{8,11}$.0$^{14,19}$]-heptacosa-1,3,5,7,9,11(27),12,14,16,18,20,22(25),23-tridecaene-16(1-oxy)hexylphosphoramidite, cpd. $2_B$. To the solid Dy complex prepared above (104 mg, 0.1129 mmol) under a strict nitrogen atmosphere was added anhydrous dichloromethane (4 mL) followed by N,N-diisopropylethylamine (79 µL, 0.4515 mmol). The system was cooled to 0° C. and 2-cyanoethyl-N,N-diisopropylchlorophosphoramidite (76 µL, 0.3386 mmol) was added via syringe. After 3.5 h, the reaction was quenched using anhydrous methanol (416 µL), and diluted using methylene chloride (8 mL). The solution was washed with saturated sodium bicarbonate (12 mL), followed by saturated sodium chloride (10 mL). The organic layer was concentrated to a volume of approximately 2 mL and added dropwise to vigorously stirring diethyl ether (46 mL). The resulting solid was isolated by centrifugation (2000 rpm, 5 min.) and washed with diethyl ether (3×46 mL), isolating the solid after each wash by centrifugation. Solvents were removed under reduced pressure to yield the title compound $2_B$ as a deep green solid (80 mg).

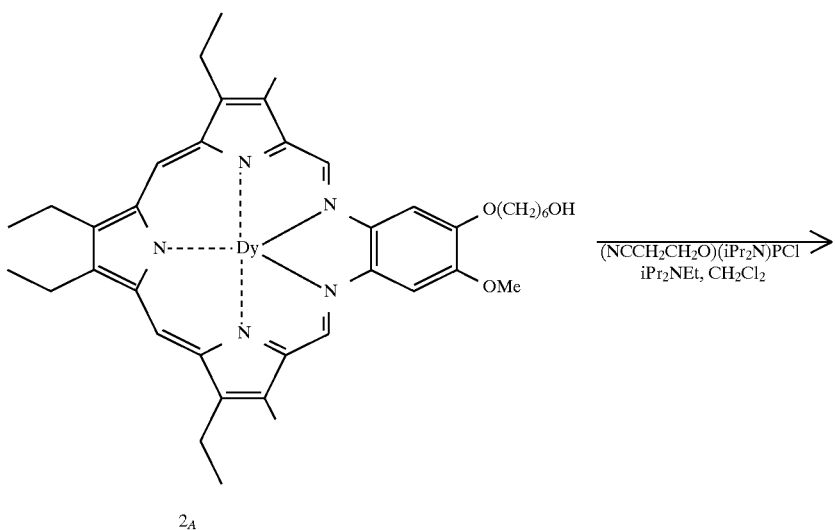

$2_A$

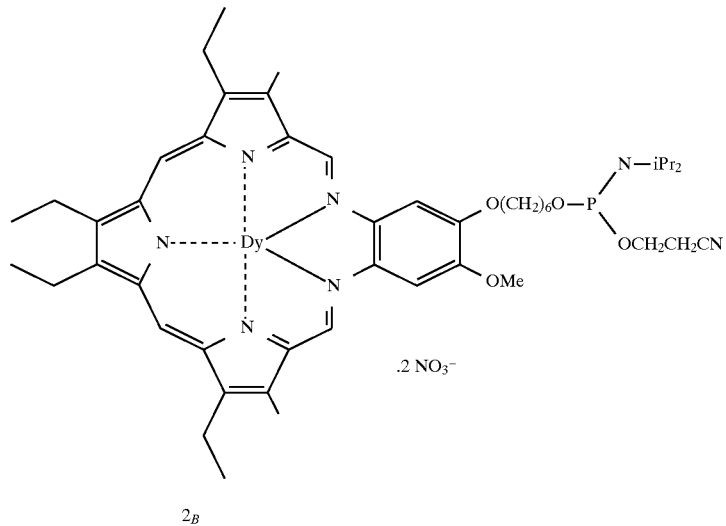

$2_B$

EXAMPLE 3

Preparation of a Dual Texaphyrin Phosphoramidite

Following the procedures of Example 2, a dual texaphyrin phosphoramidite $3_B$ may be prepared from the DyTx complex $3_A$ (2 eq.).

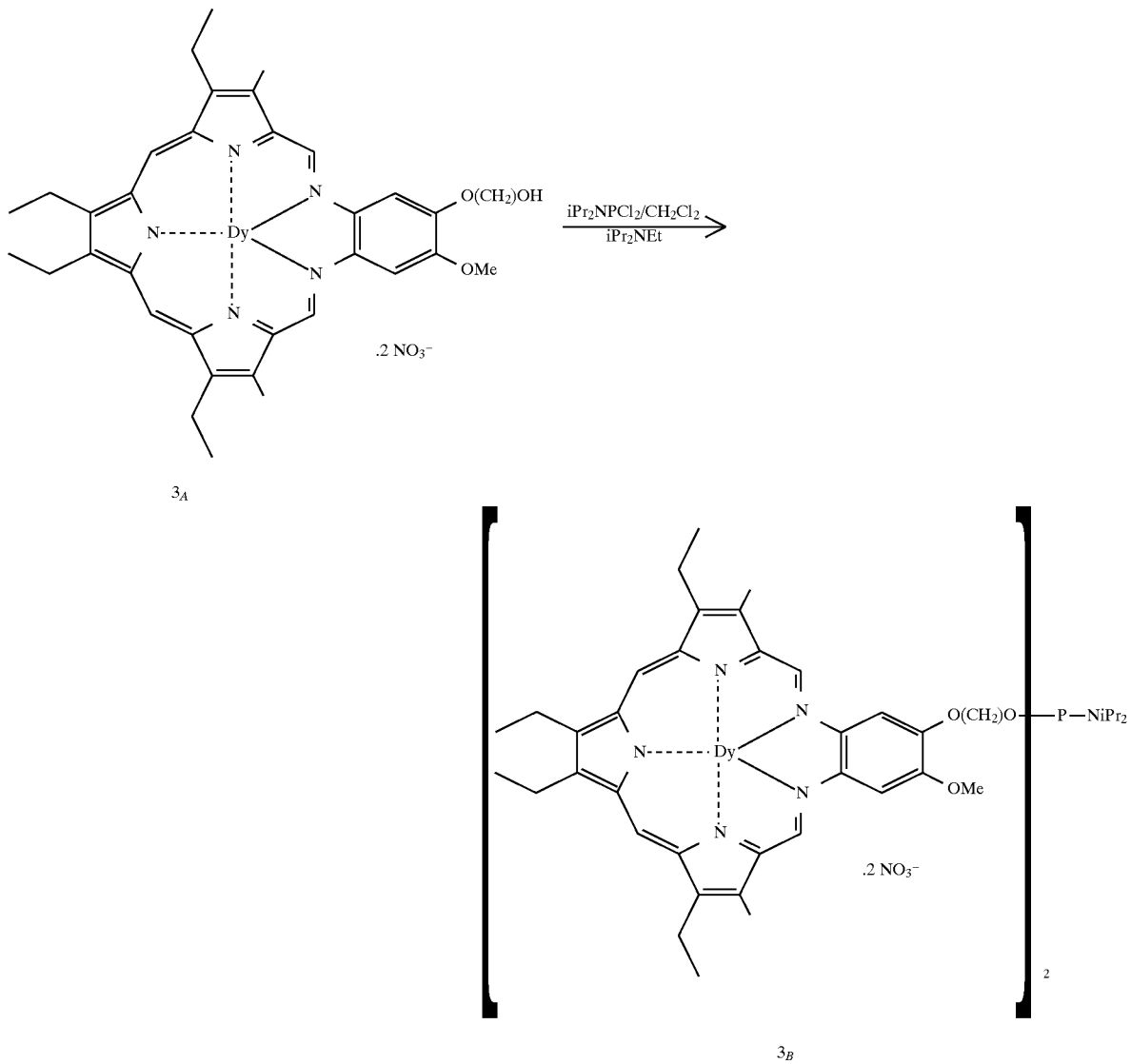

Such a dual texaphyrin phosphoramidite is useful in preparing a texaphyrin-oligonucleotide conjugate having two texaphyrin macrocycles at the terminus of the oligonucleotide, which conjugate would be expected to have greater hydrolytic or photolytic cleavage activity of an RNA or DNA, for example.

EXAMPLE 4

Preparation of a Sapphyrin Phosphoramidite

A sapphyrin phosphoramidite derivative for use in coupling to a nucleotide according to the methods described herein was prepared as follows.

8-[3-(di-(p-anisoyl)phenylmethyloxy)propyl]-17-[3-(2-cyanoethoxy-N,N-di-(isopropyl)amino(oxy)phosphine) propyl]-3,12,13,22-tetraethyl-2,7,18,23-tetramethylsapphyrin, cpd. $4_B$. The sapphyrin $4_A$ (56.5 mg, 0.05870 mmol) was dried under high vacuum for 15 h in a 25 mL round-bottom flask also containing a stir bar. Under a strict nitrogen atmosphere, methylene chloride (6 mL, freshly distilled over $P_2O_5$) was added. To the resulting suspension was added N,N-di-(isopropyl)ethylamine (24 µL, 0.1371 mmol), 2-cyanoethyl-N,N,N',N'-tetra-(isopropyl)phosphorodiamidite (60 µL, 0.1870 mmol) and 1H-tetrazole (5.0 mg, 0.0686 mmol). After stirring for 1 h, the reaction was diluted with methylene chloride (6 mL). After a further 1 h of stirring, N,N-di(isopropyl)ethylamine (24 µL, 0.1371 mmol), 2-cyanoethyl-N,N,N',N'-tetra-(isopropyl)phosphorodiamidite (60 µL, 0.1870 mmol) and 1H-tetrazole (5.0 mg, 0.0686 mmol) were added. After a total of 3.5 h, N,N-di-(isopropyl)ethylamine (24 mL, 0.1371 mmol) and 2-cyanoethyl-N,N,N',N'-tetra-(isopropyl) phosphorodiamidite (60 µL, 0.1870 mmol) were added. After 6 h, the homogeneous reaction mixture was washed with a saturated solution of sodium bicarbonate (11 mL) for 2 min, and then with a saturated solution of sodium chloride (11 mL) for 2 min. The organic phase was dried over anhydrous magnesium sulphate for 5 min and then concentrated by rotary evaporation under reduced pressure to a volume of 950 µL. The solution of the crude sapphyrin phosphoramidite in methylene chloride was dripped into hexanes (50 mL) using a 1 mL gas-tight syringe which was rinsed with methylene chloride (100 µL). After stirring for 5 min, the fine precipitate was filtered and the resulting solid was dried under high vacuum for 3 h. A 50 mM solution of the phosphoramidite in methylene chloride was prepared and filtered through a 0.2 micron nylon membrane into a 5 mL vial suitable for use with an automated DNA synthesizer. The solvent was removed by the passage of a nitrogen stream over the solution, and the resulting solid was further dried under high vacuum for 18 h to yield the title compound $4_B$ (48 mg, 70%).

12,18-diethyl-3,7,8,13,17-pentamethylporphyrin-2-[N-(3-(2-cyanoethoxy-N,N-di-(isopropyl)amino(oxy)phosphine)propyl)propionamide], cpd. $6_B$. The porphyrin alcohol $6_A$ (40 mg, 0.0707 mmol; prepared according to the protocol of Thuong and Asseline, Chapter 12 in *Oligonucleotides and Analogues A Practical Approach*, F. Eckstein, Ed., IRL Press, NY, 1991) was dried under high vacuum for 15 h in a 25 mL round-bottom flask also containing a stir bar. Under a strict nitrogen atmosphere methylene chloride (14 mL, freshly distilled over $P_2O_5$) was added. To the resulting suspension was added N,N-di-(isopropyl)ethylamine (27 µL, 0.1555 mmol), 2-cyanoethyl-N,N,N',N'-tetra-(isopropyl)phosphorodiamidite (68 µL, 0.2121 mmol) and 1H-tetrazole (5.5 mg, 0.0778 mmol). After stirring for 2 h,

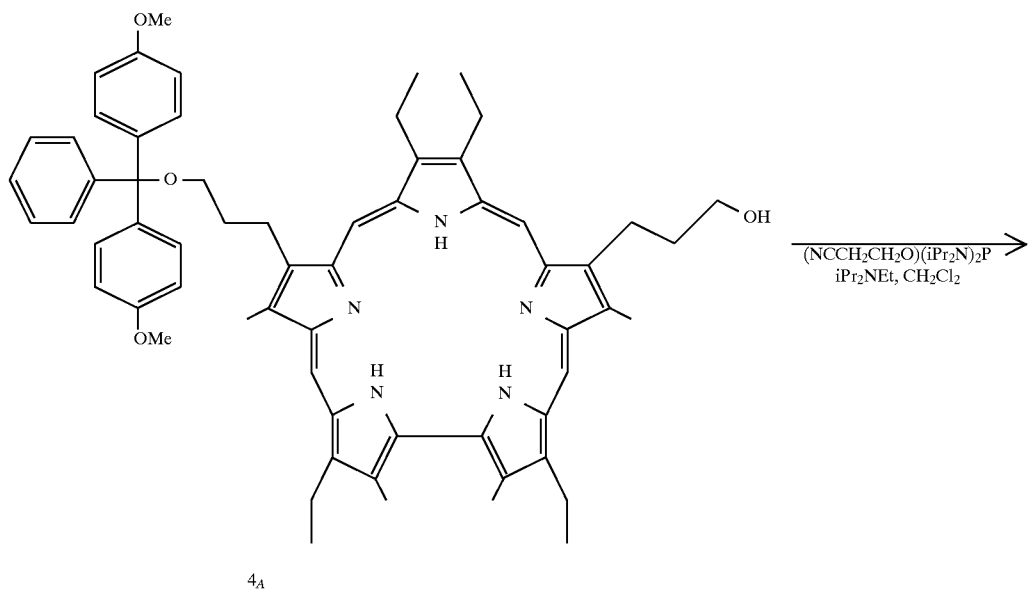

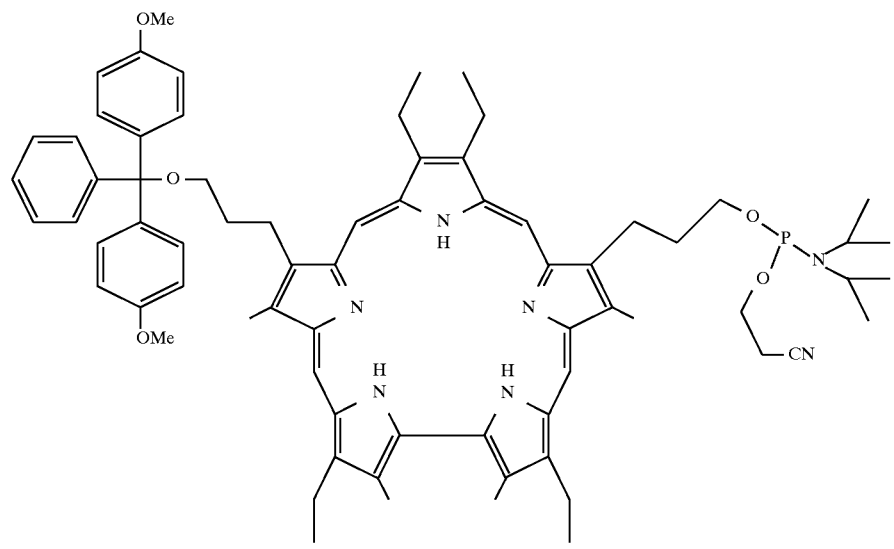

EXAMPLE 5

Preparation of a Porphyrin Phosphoramidite

A porphyrin phosphoramidite derivative for use in coupling to a nucleotide according to the methods described herein was prepared as follows.

N,N-di-(isopropyl)ethylamine (27 µL, 0.1555 mmol), 2-cyanoethyl-N,N,N',N'-tetra-(isopropyl)phosphorodiamidite (68 µL, 0.2121 mmol) and 1H-tetrazole (5.5 mg, 0.0778 mmol) were added. After a total of 4 h, the homogeneous reaction mixture was washed with a saturated solution of sodium bicarbonate (11 mL) for 2 min, and then with a saturated solution of sodium chloride for 2 min. The organic phase was dried over anhydrous magnesium sulphate for 5 min and then concentrated by rotary evaporation under reduced pressure to a volume of 650 μL. The solution of the crude porphyrin phosphoramidite in methylene chloride was dripped in to hexanes (50 mL) using a 1 mL gas-tight syringe which was rinsed with methylene chloride (100 μL). After stirring for 5 min, the fine precipiatate was filtered and the resulting solid was dried under high vacuum for 3 h. A 50 mM solution of the phosphoramidite in methylene chloride was prepared and filtered through a 0.2 micron nylon membrane into a 5 mL vial suitable for use with an automated DNA synthesizer. The solvent was removed by the passage of a nitrogen stream over the solution, and the resulting solid was further dried under high vacuum for 18 h to yield the phosphoramidite derivative $6_B$ (40 mg, 75%).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods, and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

What is claimed is:

1. A phosphoramidite derivative of an expanded porphyrin.

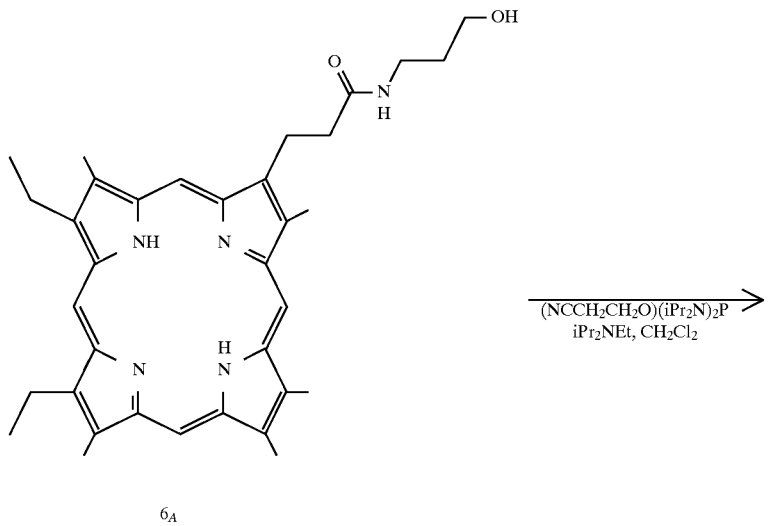

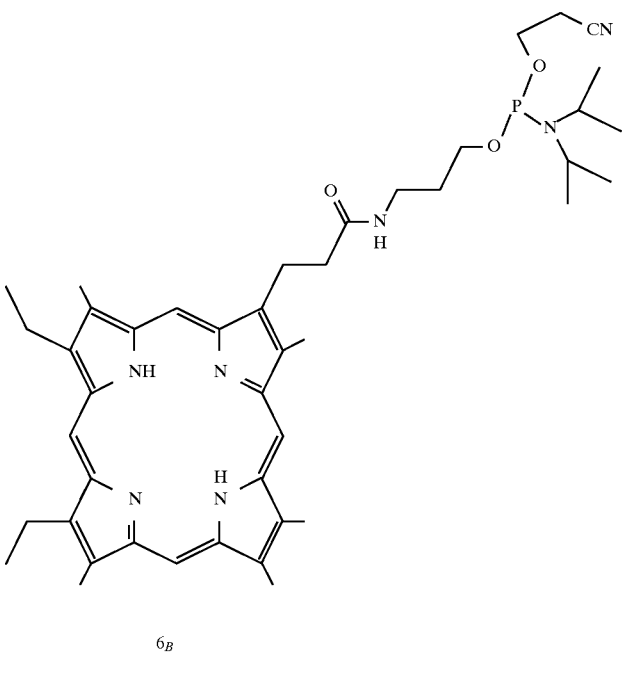

2. A phosphoramidite derivative of a sapphyrin.

3. A phosphoramidite derivative of a sapphyrin, said derivative having the following formula III:

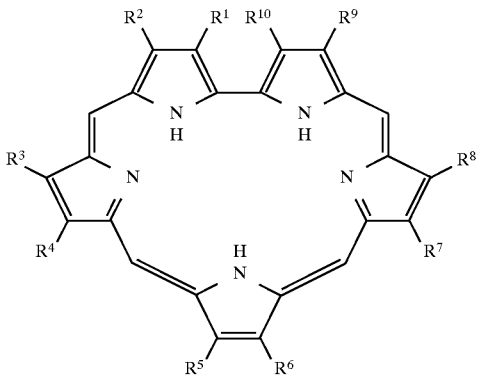

III wherein,
each of $R^1$–$R^{10}$ is independently selected from hydrogen, alkyl, alkenyl, alkynyl, halo, haloalkyl, hydroxyalkyl, glycol, polyglycol, thiol, alkyl thiol, aminoalkyl, carboxyalkyl, alkoxyalkyl, aryloxyalkyl, alkyloxycarbonyl, aryloxycarbonyl, CHO—, an ether group, a ketone group, carboxyl, phosphate, phosphonate, sulfate, phosphate-substituted alkyl, phosphonate-substituted alkyl, sulfate-substituted alkyl, phosphoramidityl, alkylphosphoramidityl, alkoxyphosphoramidityl, the group —$(CH_2)_t$—O—W where W is hydrogen or a protecting group and t is an integer less than or equal to 10, or the group —$(CH_2)_x$—A—$(CH_2)_y$—B, where A is $CH_2$, O, S, NH or $NR^{11}$, where $R^{11}$ is alkyl, alkenyl, alkynyl, halo, haloalkyl, hydroxyalkyl, glycol, polyglycol, thiol, alkyl thiol, aminoalkyl, carboxyalkyl, alkoxyalkyl, aryloxyalkyl, alkyloxycarbonyl, aryloxycarbonyl, CHO—, an ether group a ketone group, carboxyl phosphate, phosphonate, sulfate, phosphate-substituted alkyl, phosphonate-substituted alkyl, or sulfate-substituted alkyl, COO, CONH, CSNH, or $CONR^{11}$; B is selected from the values of A, aryl, silyl, siloxy, aminoaryl, amino, amidoaryl, sugar, sugar derivative, polysaccharide, metal chelating group, alkylating agent, steroid, steroid derivative, amino acid, peptide, or polypeptide; and each of x and y is independently an integer of less than or equal to 10 or are zero; with the proviso that one of $R^1$–$R^{10}$ is phosphoramidityl, alkylphosphoramidityl, or alkoxyphosphoramidityl.

4. A phosphoramidite derivative of a sapphyrin according to claim 3 wherein one of $R^1$–$R^{10}$ is alkylphosphoramidityl or alkoxyphosphoramidityl, and the others of $R^1$–$R^{10}$ are independently alkyl, hydroxyalkyl or the group —$(CH_2)_t$—O—W.

5. A phosphoramidite derivative of a sapphyrin according to claim 3 wherein one of $R^1$–$R^{10}$ is alkylphosphoramidityl where the alkyl of the alkylphosphoramidityl has from one to ten carbon atoms.

6. A phosphoramidite derivative of a sapphyrin according to claim 5 wherein the alkyl of the alkylphosphoramidityl has from three to six carbon atoms.

7. A phosphoramidite derivative of a sapphyrin according to claim 3 wherein one of $R^1$–$R^{10}$ is alkoxyphosphoramidityl where the alkoxy of the alkoxyphosphoramidityl has from one to ten carbon atoms.

8. A phosphoramidite derivative of a sapphyrin according to claim 7 wherein the alkoxy of the alkoxyphosphoramidityl has from three to six carbon atoms.

9. A phosphoramidite derivative of a sapphyrin having the following formula:

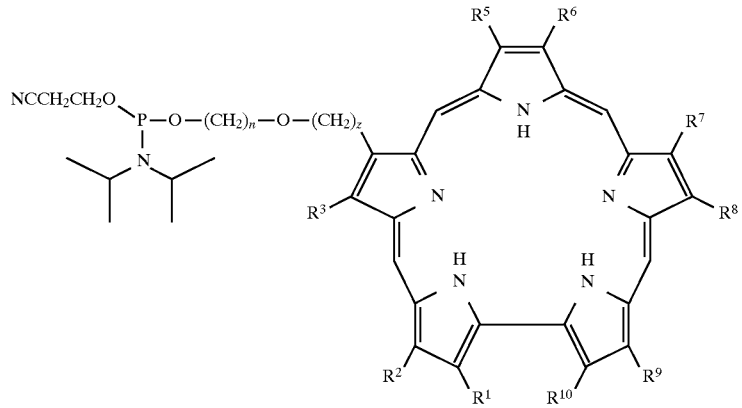

wherein,
n is zero or an integer less than or equal to 10;
z is an integer less than or equal to 10; and
each of $R^1$–$R^3$ and $R^5$–$R^{10}$ is independently selected from hydrogen, alkyl, alkenyl, alkynyl, halo, haloalkyl, hydroxyalkyl, glycol, polyglycol, thiol, alkyl thiol, aminoalkyl, carboxyalkyl, alkoxyalkyl, aryloxyalkyl, alkyloxycarbonyl, aryloxycarbonyl, CHO—, an ether group, a ketone group, carboxyl, phosphate, phosphonate, sulfate, phosphate-substituted alkyl, phosphonate-substituted alkyl, sulfate-substituted alkyl, the group —$(CH_2)_t$—O—W where W is hydrogen or a protecting group and t is an integer less than or equal to 10, or the group —$(CH_2)_x$—A—$(CH_2)_y$—B, where A is $CH_2$, O, S, NH or $NR^{11}$, where $R^{11}$ is alkyl, alkenyl, alkynyl, halo, haloalkyl, hydroxyalkyl, glycol, polyglycol, thiol, alkyl thiol, aminoalkyl, carboxyalkyl, alkoxyalkyl, aryloxyalkyl, alkyloxycarbonyl, aryloxycarbonyl, CHO—, an ether group, a ketone group, carboxyl, phosphate, phosphonate, sulfate, phosphate-substituted alkyl, phosphonate-substituted alkyl, or sulfate-substituted alkyl, COO, CONH, CSNH, or $CONR^{11}$; B is selected from the values of A, aryl, silyl, siloxy, aminoaryl, amino, amidoaryl, sugar, sugar derivative, polysaccharide, metal chelating group, alkylating agent, steroid, steroid derivative, amino acid, peptide, or polypeptide; and each of x and y is independently an integer of less than or equal to 10 or are zero.

10. A phosphoramidite derivative of a sapphyrin according to claim 9 where each of $R^1$–$R^3$, $R^5$, $R^6$ and $R^8$–$R^{10}$ is independently alkyl; and $R^7$ is alkyl, hydroxyalkyl or the group —$(CH_2)_t$—O—W.
11. A phosphoramidite derivative of a sapphyrin according to claim 9, having the following formula:
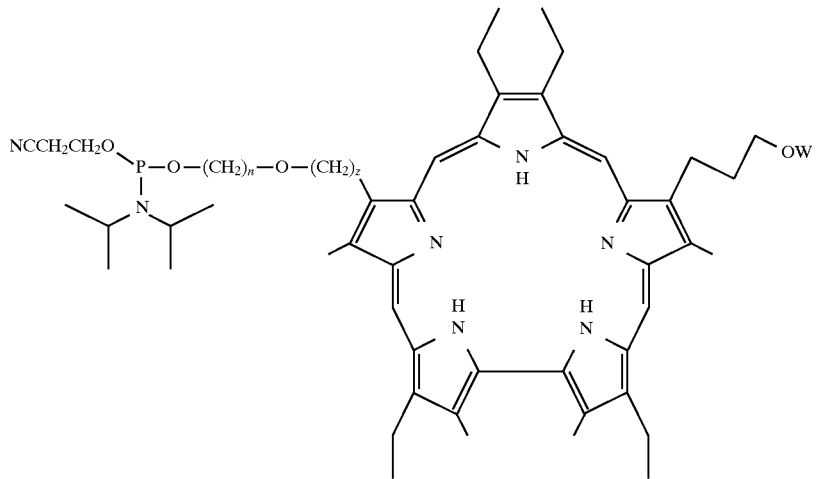
wherein, n is zero or an integer less than or equal to 10 and z is an integer less than or equal to 6.
12. A phosphoramidite derivative of a porphyrin.
* * * * *